(12) United States Patent
Song et al.

(10) Patent No.: US 9,581,545 B2
(45) Date of Patent: Feb. 28, 2017

(54) OPTICAL SENSING SYSTEM AND METHOD OF DETERMINING A CHANGE IN A REFRACTIVE INDEX IN AN OPTICAL SENSING SYSTEM

(71) Applicant: AGENCY FOR SCIENCE, TECHNOLOGY AND RESEARCH, Singapore (SG)

(72) Inventors: Junfeng Song, Singapore (SG); Xianshu Luo, Singapore (SG); Xiaoguang Tu, Singapore (SG); Qing Fang, Singapore (SG); Guo-Qiang Patrick Lo, Singapore (SG); Mingbin Yu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 7 days.

(21) Appl. No.: 14/434,399

(22) PCT Filed: Oct. 8, 2013

(86) PCT No.: PCT/SG2013/000431
§ 371 (c)(1),
(2) Date: Apr. 8, 2015

(87) PCT Pub. No.: WO2014/058391
PCT Pub. Date: Apr. 17, 2014

(65) Prior Publication Data
US 2015/0268161 A1    Sep. 24, 2015

(30) Foreign Application Priority Data

Oct. 8, 2012   (SG) ................................ 201207485-2

(51) Int. Cl.
*G01N 21/41*   (2006.01)
*G01N 21/77*   (2006.01)

(52) U.S. Cl.
CPC ......... *G01N 21/41* (2013.01); *G01N 21/7746* (2013.01); *G01N 2021/7716* (2013.01); *G01N 2021/7776* (2013.01)

(58) Field of Classification Search
CPC .......... H01S 5/00; H01S 3/00; H01S 2301/00; G02F 1/00; H04B 10/00; G01N 21/41; G01N 21/7746

(Continued)

(56) References Cited

U.S. PATENT DOCUMENTS 7,697,121 B1 *   4/2010   Coroy .................... G01B 11/18
                                                           356/35.5
2003/0039013 A1 *   2/2003   Jones ...................... H03L 7/087
                                                           398/147

(Continued)

OTHER PUBLICATIONS

Xudong Fan, et al., "Sensitive Optical Biosensors for Unlabeled Targets: A Review", Analytica Chimica Acta, vol. 620, pp. 8-26, (2008).

(Continued)

*Primary Examiner* — Tarifur Chowdhury
*Assistant Examiner* — Isiaka Akanbi
(74) *Attorney, Agent, or Firm* — Blakely Sokoloff Taylor & Zafman LLP

(57) ABSTRACT

An optical sensing system may include a light separation element configured to separate an input light into a plurality of sliced lights and a first resonator configured to receive one sliced light of the plurality of sliced lights. An effective refractive index of the first resonator may be changeable in response to a change in a refractive index of a cladding of the first resonator, a second resonator coupled to the first resonator and a detector configured to measure an intensity of the sliced light, the intensity of the sliced light based on a difference between a resonant wavelength of the first resonator and a resonant wavelength of the second resonator.

(Continued)

The difference between a resonant wavelength of the first resonator and a resonant wavelength of the second resonator may be based on the effective refractive index of the first resonator.

18 Claims, 23 Drawing Sheets

(58) Field of Classification Search
USPC .......................... 356/128, 328; 385/122, 16
See application file for complete search history.

(56) References Cited

U.S. PATENT DOCUMENTS

| | | | |
|---|---|---|---|
| 2012/0177060 A1* | 7/2012 | Lipson ............... | G02B 6/12007 370/464 |
| 2012/0194803 A1 | 8/2012 | Song et al. | |
| 2013/0242400 A1* | 9/2013 | Chen ...................... | G01S 17/42 359/618 |
| 2014/0092375 A1* | 4/2014 | Raghavan ............... | G01L 1/246 356/32 |

OTHER PUBLICATIONS

Junfeng Song, et al., "An Optical Sensing System and a Method of Determining a Change in an Effective Refractive Index of a Resonator of an Optical Sensing System", Singapore Patent Application No. 2011096997, 46 pp., (Dec. 28, 2011).

Qing Fang, et al., "High Efficiency Ring-Resonator Filter with NiSi Heater", IEEE Photonics Technology Letters, vol. 24, No. 5, pp. 350-352, (Mar. 1, 2012).

PCT Notification of Transmittal of the International Search Report and the Written Opinion of the International Searching Authority, or the Declaration for PCT Counterpart Application No. PCT/SG2013/000431, 10 pp., (Dec. 4, 2013).

PCT International Preliminary Report on Patentability (Chapter II of the Patent Cooperation Treaty) for PCT Counterpart Application No. PCT/SG2013/000431, 26 pp., (Jul. 25, 2014).

Charis Mesaritakis, et al., "Adaptive Interrogation for Fast Optical Sensing Based on Cascaded Micro-Ring Resonators", IEEE Sensors Journal, vol. 11, No. 7, pp. 1595-1601, (Jul. 2011).

Kenichi Iga, et al., "Arrayed Waveguide Grating", Encyclopedic Handbook of Integrated Optics, CRC Press, 22 pp. (including cover page, table of contents, and pp. 16-23), (2006).

Junfeng Song, et al., "Electrical Tracing-Assisted Dual-Microring Label-Free Optical Bio/Chemical Sensors", Optics Express, vol. 20, No. 4, pp. 4189-4197, (Feb. 13, 2012).

* cited by examiner

- separate an input light into a plurality of sliced lights  
  — 702

- coupleone sliced light of the plurality of sliced lights though a first resonator of a plurality of first resonators to one detector of a plurality of detectors of the optical sensing system  
  — 704

- place a sample in contact with the first resonator,  
  — 706

- measure a change in an intensity of the sliced light by the detector due to the sample being placed in contact with the first resonator, the change in intensity based on a change in a difference between a resonant wavelength of the first resonator and a resonant wavelength of a second resonator  
  — 708

- determine the change in an effective refractive index of the first resonator based on the change in the intensity of the sliced light  
  — 710

OPTICAL SENSING SYSTEM AND METHOD OF DETERMINING A CHANGE IN A REFRACTIVE INDEX IN AN OPTICAL SENSING SYSTEM

CROSS-REFERENCE TO RELATED APPLICATIONS

This patent application is a U.S. National Phase Application under 35 U.S.C. §371 of International Application No. PCT/SG2013/000431, filed Oct. 8, 2013, entitled OPTICAL SENSING SYSTEM AND METHOD OF DETERMINING A CHANGE IN A REFRACTIVE INDEX IN AN OPTICAL SENSING SYSTEM, which claims the benefit of priority of Singapore Patent Application No. 201207485-2, filed Oct. 8, 2012, the contents of which were incorporated by reference in their entirety for all purposes.

TECHNICAL FIELD

Various aspects of this disclosure relate to an optical sensing system and methods of determining a change in a refractive index in an optical sensing system.

BACKGROUND

Label-free optical biological/chemical sensors are essential in the application of medical diagnosis, healthcare and environmental monitoring etc. Among all the approaches, optical microresonator-based biosensors are regarded to be very promising due to their high sensitivity to refractive index change ($\sim10^{-4}$-$10^{-7}$ refractive index unit (RIU)), which are comparable to the sensitivity of conventional surface plasmon resonance (SPR) technique. In addition, optical microresonator-based biosensors typically have compact footprint ($\sim$10's µm-$\sim$100's µm), and offer potential large-scale integration with microfluidics.

Single microring resonator-based biosensors in silicon-on-insulator (SOI) have been demonstrated using either conventional microrings. The demonstrated detection limit ranges from $10^{-5}$-$10^{-7}$ RIU.

However, for nearly all the demonstrated microresonator sensors, the wavelength-scanning method using wavelength-tunable lasers was considered to be the "default" technique for measuring sharp resonant wavelength shift. The wavelength-scanning method requires high-resolution wavelength tunable lasers in order to measure the sharp resonant wavelength shift, in which the detection limit is limited by the laser resolution. Furthermore, high-resolution wavelength-scanning lasers are very expensive and not suitable for point-of-care applications.

SUMMARY

In various embodiments, an optical sensing system is provided. The optical sensing system may include a light separation element configured to separate an input light into a plurality of sliced lights. The optical sensing system may further include a first resonator configured to receive one sliced light of the plurality of sliced lights. An effective refractive index of the first resonator may be changeable in response to a change in a refractive index of a cladding of the first resonator. The optical sensing system may also include a second resonator coupled to the first resonator. The optical sensing system may further include a detector configured to measure an intensity of the sliced light, the intensity of the sliced light based on a difference between a resonant wavelength of the first resonator and a resonant wavelength of the second resonator. The difference between a resonant wavelength of the first resonator and a resonant wavelength of the second resonator may be based on the effective refractive index of the first resonator.

In various embodiments, a method of determining a change in an effective refractive index of a first resonator in an optical sensing system may be provided. The method may include separating an input light into a plurality of sliced lights. The method may further include coupling one sliced light of the plurality of sliced lights though a first resonator of a plurality of first resonators to one detector of a plurality of detectors of the optical sensing system. The method may also include placing a sample in contact with the first resonator. The method may also include measuring a change in an intensity of the sliced light by the detector due to the sample being placed in contact with the first resonator. The change in intensity may be based on a change in a difference between a resonant wavelength of the first resonator and a resonant wavelength of a second resonator. The method may further include determining the change in an effective refractive index of the first resonator based on the change in the intensity of the sliced light.

BRIEF DESCRIPTION OF THE DRAWINGS

The invention will be better understood with reference to the detailed description when considered in conjunction with the non-limiting examples and the accompanying drawings, in which:

FIG. 7 is a schematic illustrating a method of determining a change in one or more effective refractive indexes in an optical sensing system according to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

Figure 1A:
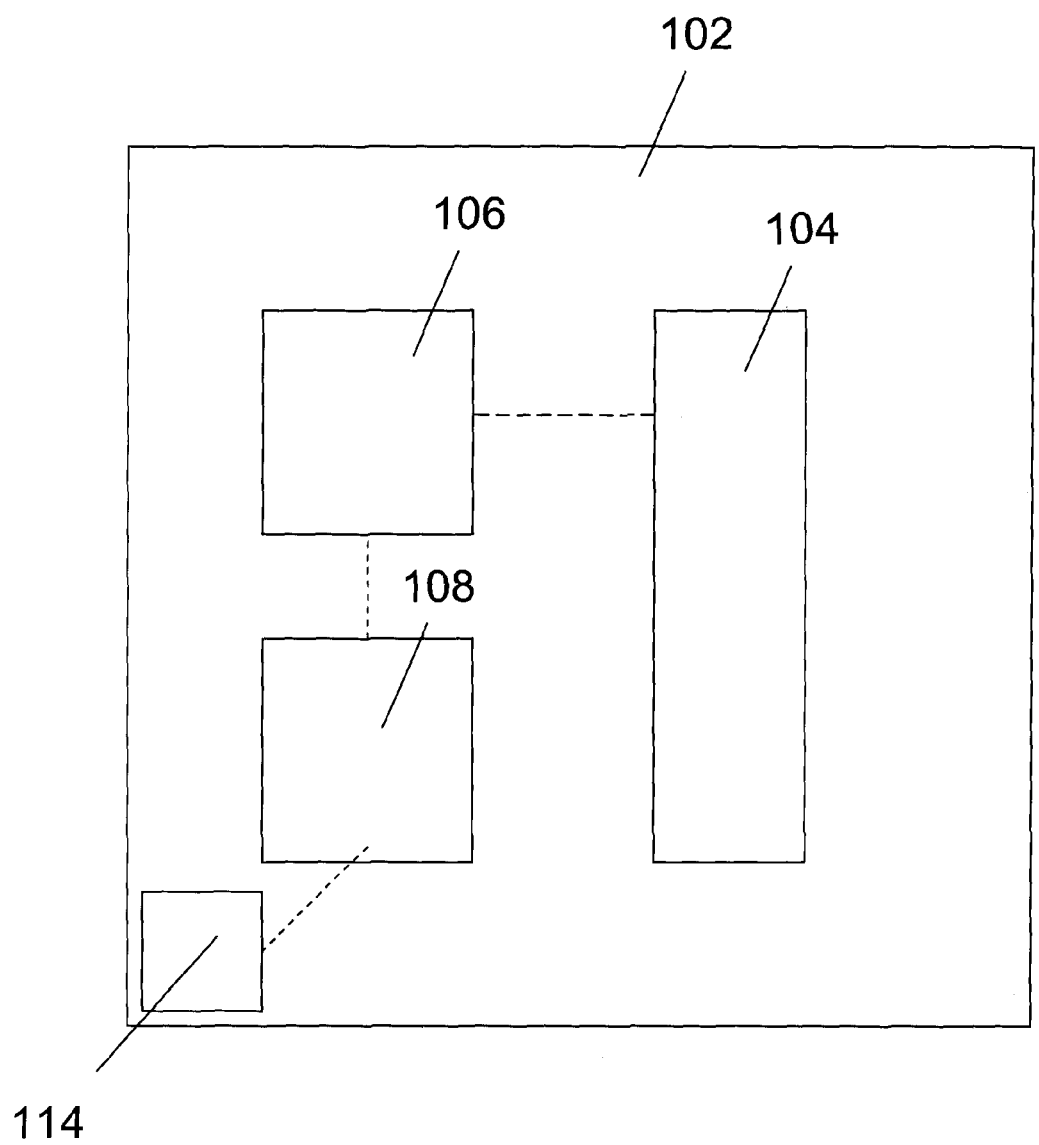
FIG. 1A is a schematic showing an optical sensing system according to various embodiments.

FIG. 1A is a schematic 100 showing an optical sensing system 102 according to various embodiments. The optical sensing system 102 may include a light separation element 104 configured to separate an input light into a plurality of sliced lights. The optical sensing system 102 may further include a first resonator 106 configured to receive one sliced light of the plurality of sliced lights. An effective refractive index of the first resonator 106 may be changeable in response to a change in a refractive index of a cladding of the first resonator 106. In addition, the optical sensing system 102 may include a second resonator 108 coupled to the first resonator 106. The optical sensing system 102 may further include a detector 114 configured to measure an intensity of the sliced light. The intensity of the sliced light may be based on a difference between a resonant wavelength of the first resonator 106 and a resonant wavelength of the second resonator 108. The difference between the resonant wavelength of the first resonator 106 and the resonant wavelength of the second resonator 108 may be based on an effective refractive index of the first resonator 106.

In other words, the optical sensing system may include a light separation element 104 configured to separate an input light into a plurality of component lights. One component light of the plurality of component lights may be coupled to a first resonator 106. The effective refractive index of the first resonator 106 may be dependent on the surroundings in which the first resonator 106 is placed in, such as a sample in which the first resonator 106 is in contact with. The optical sensing system may further include a detector 114 configured to measure an intensity of the sliced light. The intensity of the sliced light may be dependent on the difference between the resonant wavelength of the first resonator 106 and the resonant wavelength of the second resonator 108. The resonant wavelength of the first resonator 106 may be in turn be dependent on the effective refractive index of the first resonator 106.

Figure 1B:
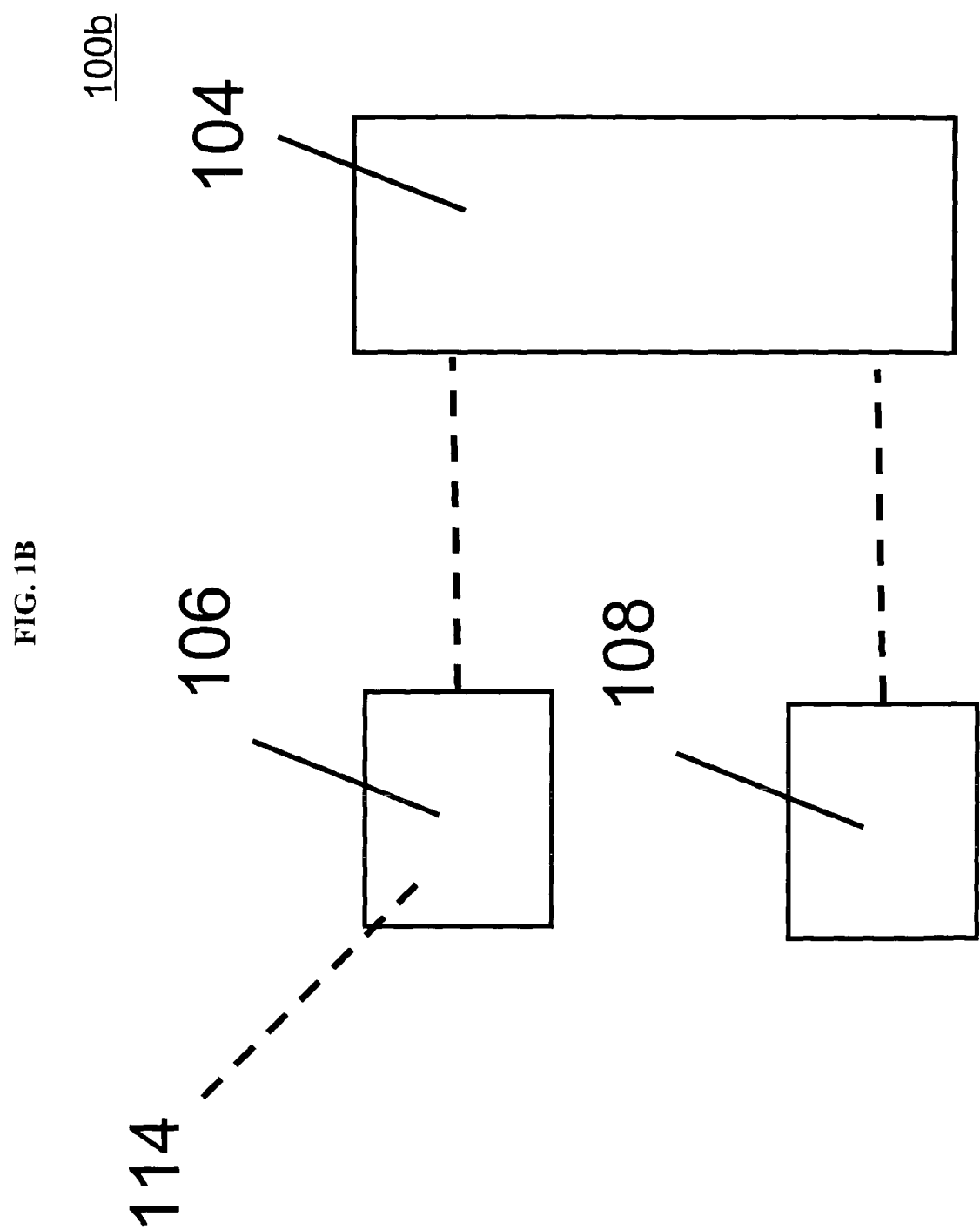
FIG. 1B is another schematic showing an optical sensing system according to various embodiments.
Figure 1C:
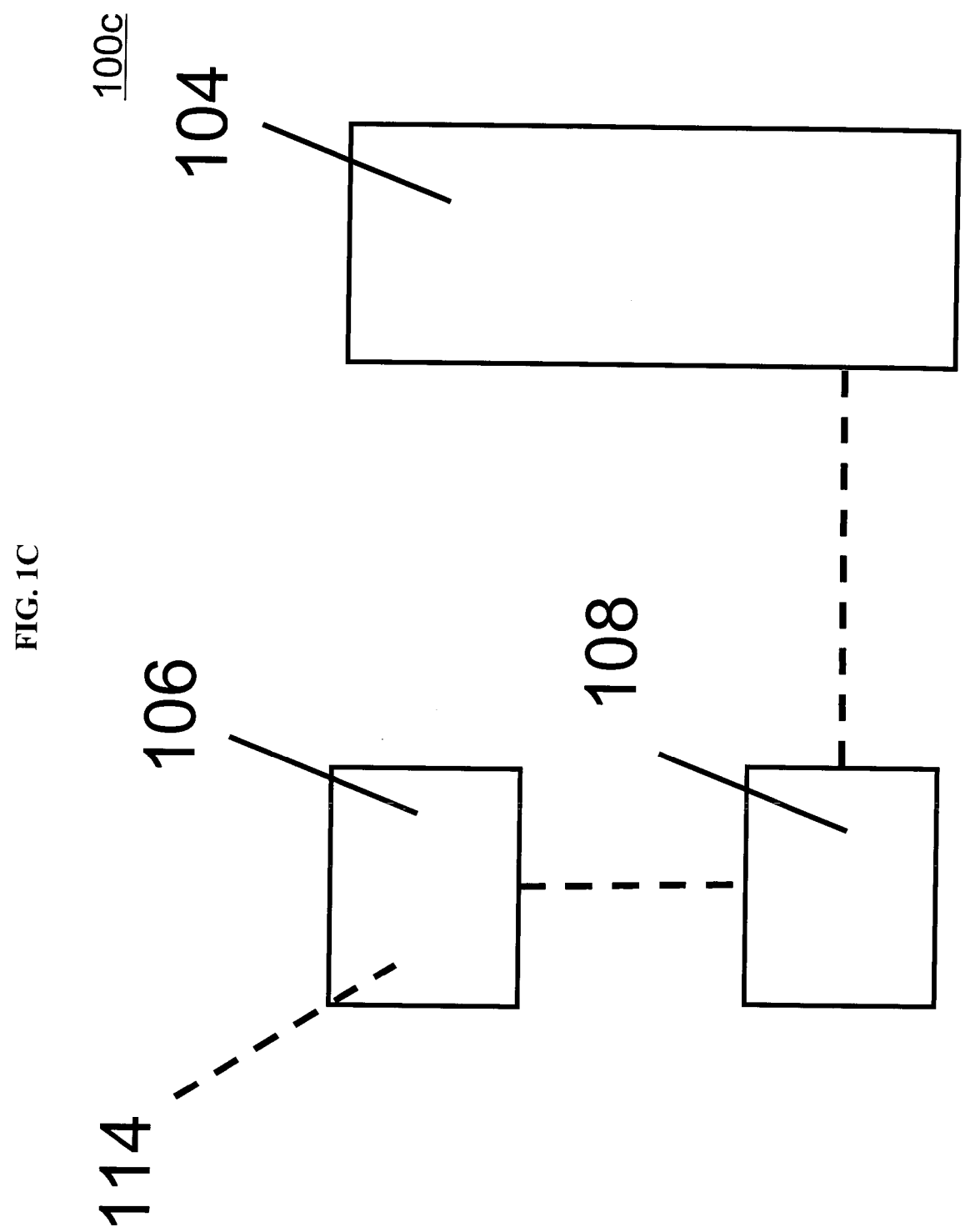
FIG. 1C is a further schematic showing an optical sensing system according to various embodiments.

The different optical elements such as the light separation element 104, the first resonator 106 and the second resonator 108 may be coupled to one another in different manners. FIG. 1B is another schematic 100b showing an optical sensing system according to various embodiments. FIG. 1C is a further schematic 100c showing an optical sensing system according to various embodiments.

Coupling between a first element and a second element may include direct coupling between the first element and the second element or indirect coupling between the first optical element and the second optical element via one or more further elements. The one or more elements further may include waveguides and/or optical fibers as well as other optical elements. For avoidance of doubt, the dotted lines in FIGS. 1A-C may represent direct coupling or indirect coupling.

In various embodiments, the difference between the resonant wavelength of the first resonator 106 and the resonant wavelength of the second resonator 108 may be based on the resonant wavelength of the first resonator 106 and the resonant wavelength of the second resonator 108. The resonant wavelength of the first resonator 106 may be based on the effective refractive index of the first resonator 106.

In various embodiments, the resonant wavelength of the second resonator 108 may be adjustable to a current or voltage applied to the second resonator 108.

In various embodiments, if the resonant wavelength of the second resonator is kept unchanged, the change in the difference (between the resonant wavelength of the first resonator 106 and the resonant wavelength of the second resonator 108) nay be based on a change in the effective refractive index of the first resonator 106. Further, if the change or shift in the resonant wavelength of the first resonator 106 may be based on the change in the effective refractive index of the first resonator 106.

In various embodiments, the optical sensing system 102 may be a biological/chemical sensor.

In various embodiments, the first resonator 106 may serve as the sensing element and the second resonator 108 may serve as the tracing element.

In various embodiments, the optical sensing system 102 may be a microring resonator-based optical sensor or sensing system. The resonators may be microring resonators.

The optical sensing system 102 may include one or more microring resonators serving as the sensing element or sensing elements. The optical sensing system 102 may include one or more microring resonators serving as the tracing element or tracing elements.

The optical sensing system 102 may include similarly designed resonators to serve as sensing elements and tracing elements. The first resonator 106 may serve as a sensing element. The second resonator 108, which is similarly designed as the first resonator 106, may serve as a tracing element. The first resonator 106 may be used for sensing. The second resonator 108 may be used for tracking or responding to any changes in the properties, e.g. effective refractive index, of the first resonator 106. For instance, the first resonator 106 may be configured to contact a biological or chemical sample. The second resonator 108 may be used to track or respond to changes in properties of the first resonator 106 as a result of a stimulus, e.g. coming into contact with the biological sample or chemical sample. In various embodiments, the first resonator 106 may include an underlying layer. The underlying layer may include silicon. Additionally, or alternatively, the underlying layer may include silicon nitride, silicon oxynitride or silicon oxide. The second resonator 108 may be similar to the first resonator 106 but without an underlying layer. The absence of an underlying layer for the second resonator 108 may enhance heat confinement, leading to ultralow power consumption for the second resonator 108. With the underlying layer, power consumption may be relatively high, with up to 10s of mW for a conventional sensing. The first resonator 106 and the second resonator 108 may be configured to have the same separation between successive resonant wavelengths. In various embodiments, one resonant wavelength may correspond to one resonant frequency. When the first resonator 106 and the second resonator 108 have the same resonant wavelengths, the first resonator 106 and the second resonator 108 also have the same resonant frequencies. In this context, "resonant wavelength" and "resonant frequency" may be used interchangeably.

Sliced lights in the current context may refer to component lights or constituent lights or channels. An input light may be separated into a plurality of sliced light (i.e. component lights or constituent lights or channels) by the light separation element 104. The input light may be referred to as unseparated light.

Each of the plurality of sliced lights has a range of wavelengths. A sliced light may have a range of wavelengths that is a subset of the range of wavelengths of the input light. The range of wavelengths of one sliced light of the plurality of sliced lights may be different from the range of wavelengths of a further sliced light of the plurality of sliced lights. In other words, the light separation element 104 may be configured to disperse the input light into component lights of different ranges of wavelengths. The input light may be generated from a broad band light source. A first sliced light passing out from the dispersion element 104 may have a different range of wavelengths from a second sliced light. The range of wavelengths of the sliced light may or may not overlap with the range of wavelengths from the further sliced light. The light separation element 104 may be a demultiplexer such as a concave grating or an array waveguide grating (AWG). The concave grating may include one or more bragg gratings.

In various embodiments, the input light may include multiple wavelengths that may be resonant to the first resonators and/or the second resonators. In other words, light transmitted through a resonator may exhibit multiple optical intensity maxima. The period or separation between two successive transmitted optical intensity maxima or resonant wavelengths in the resonator may be know as free spectral range (FSR). The first resonator 106 and the second resonator 108 may be configured to have the same FSR.

In various embodiments, the first resonator 106 and the second resonator 108 may be configured to be at resonance. When the first resonator 106 and the second resonator 108 is at resonance, the intensity of the light received by the first resonator 106 and the second resonator 108 may be at a maximum. Light received by the first resonator 106 may be a sliced light of a plurality of sliced light. The sliced light may have a range of wavelengths, which includes a particular wavelength. The particular wavelength may correspond to the resonant wavelength of the first resonator 106 and the second resonator 108. In various embodiments, light received by the second resonator 108 may be input light. The input light may also be referred to as unseparated light. The input light or unseparated light may also include the particular wavelength. In various alternate embodiments, the sliced light may also be received by the second resonator 108. In other words, as long as the light received by the first resonator 106 and the second resonator 108 includes the particular wavelength corresponding to the resonant wavelength of the first resonator 106 and the resonant wavelength of the second resonator 108, the first resonator 106 and the second resonator 108 may be at resonance.

The first resonator 106 and the second resonator 108 may be initially at resonance or near resonance (the resonant wavelength of the first resonator is within a predetermined range from the resonant wavelength of the second resonator) such that the light intensity measured by the detector is above a predetermined level. When the first resonator 106 contacts a sample such as a chemical sample or a biological sample, the effective refractive index of the first resonator may be changed, which results a shift in resonant wavelength in the first resonator. The intensity of light measured or detected by the detector 114 may be reduced. The intensity of the light may be reduced as the shifted resonant wavelength of the first detector is no longer at the resonant wavelength of the second resonator or within the predetermined range of the resonant wavelength of the second resonator. The current or voltage may then be applied to the second resonator 108 to shift the resonant wavelength of the second resonator so as to match the shift of resonant wavelength of the first resonator. The application of the current or voltage may result in the intensity of light detected or measured to be increased back to the predetermined level. The current or voltage applied may be measured to determine the change in the effective refractive index of the first resonator 106. The change in the effective refractive index of the sensing resonator may be due to a change in the refractive index of the cladding (e.g. upper cladding layer) of the second resonator 108. In various embodiments, by providing the second resonator and incorporating thermo-optical tuning or electro-optical tuning with the second resonator (e.g. the tracing resonator may be dynamically thermally tuned or electrically tuned, due to thermo-optic (TO) or electro-optic (EO) effect respectively, (e.g. free carrier dispersion effect, liquid crystal tuning, polymer tuning)), the resonant wavelength shift may be obtained or determined, for example, by directly reading or determining the current or voltage applied to the second resonator, and/or changes in the current or voltage applied. The current or voltage may be applied using a voltage/current supply source.

For TO tuning, the second resonator may include a thermal heater. Alternatively, the optical sensing system may include a thermal heater placed in proximity to the second resonator. The resonant wavelength shift of the second resonator may be obtained or determined, for example, by directly reading or determining the current or voltage applied to the thermal heater of the second resonator or optical sensing system, and/or changes in the current or voltage applied.

One or more electrical interconnections may be connected to the second resonator 108 for the application of a current or voltage. The second resonator may also include electrodes for the application of a current or voltage.

In various embodiments, the change in the effective refractive index of the first resonator and the change in the current applied to the second resonator has a relationship of $$\Delta n_{eff} = 2ARI\Delta I \frac{n_g}{\lambda_0},$$

where $\Delta n_{eff}$ is the change in the effective refractive index of the first resonator, A is thermal efficient (nm/W), R is the resistance of a thermal heater, I is the current applied to the second resonator, $\Delta I$ is the change in the current applied to the second resonator, $n_g$ is a group refractive index of the first resonator, and $\lambda_0$ is the center wavelength of the first resonator.

In various embodiments, the difference between the resonant wavelength of the first resonator and the resonant wavelength, of the second resonator may be determined based on the variation of light intensity measured by the detector 114. The intensity of light may be measured prior to the first resonator 106 contacting the sample. The intensity of light may be measured after the first resonator 106 contacting the sample. The change in intensity of light may be used to determine the shifted resonant wavelength of the first resonator 106 as a result of contacting the sample. The resonant wavelength of the second resonator 108 may be kept unchanged (i.e. by not adjusting the voltage or current applied to the second resonator 108). The change in intensity of light may be used to determine the shifted resonant wavelength based on a known relationship between the change in intensity and a change in a difference between the resonant wavelength of the first resonator 106 and the resonant wavelength of the second resonator 108.

In various embodiments, the light separation element 104 may be coupled between the first resonator 106 and the second resonator 108. The first resonator 106 may be coupled to the detector 114. The second resonator 108 may be coupled to a light source, e.g. a broadband light source. Light from the light source may be coupled by an input waveguide to the second resonator 108. The second resonator 108 may be coupled by a coupling waveguide to the light separation element 104. The light separation element 104 may be configured to separate the input light into a plurality of sliced lights, each of the plurality of sliced lights having a range of wavelengths. The optical system 102 may further include a channel waveguide to couple one sliced light of the plurality of sliced lights to the first resonator 106. The optical system 102 may also include an output waveguide configured to couple the sliced light from the first resonator 106 to the detector 114.

In various alternate embodiments, the first resonator 106 may be coupled between the light separation element 104 and the second resonator 108. The light separation element 104 may be coupled to a light source. Light from the light source may be coupled by an input waveguide to the light separation element 104. The light separation element 104 may be configured to separate the input light into a plurality of sliced lights, each of the plurality of sliced lights having a range of wavelengths. The optical system 102 may further include a channel waveguide to couple one sliced light of the plurality of sliced lights to the first resonator 106. The optical system 102 may further include one coupling waveguide to couple the sliced light from the first resonator 106 to the second resonator 108. The optical sensing system may further include an output waveguide configured to couple the sliced optical light from the second resonator 108 to the detector 114.

In various alternate embodiments, the second resonator 108 may be coupled between the light separation element 104 and the first resonator 106. The light separation element 104 may be coupled to a light source. Light from the light source may be coupled by an input waveguide to the light separation element 104. The light separation element 104 may be configured to separate the input light into a plurality of sliced lights, each of the plurality of sliced lights having a range of wavelengths. The optical system 102 may further include a channel waveguide to couple one sliced light of the plurality of sliced lights to the second resonator 108. The optical system 102 may further include one coupling waveguide to couple the sliced light from the second resonator 108 to the first resonator 106. The optical sensing system may further include an output waveguide configured to couple the sliced optical light from the first resonator 106 to the detector 114.

In various embodiments, the optical sensing system 102 may include one or more further first resonators 106. The optical sensing system may additionally include one or more further second resonators 108. The optical sensing system 102 may be configured for wavelength demultiplexing (WDM) sensing in multiple branches. Each branch may include a first resonator as a sensing element. The optical sensing system 102 may have one or more further second resonators 108 as one or more tracing elements. The light separation element 104 may be configured to separate input light into a plurality of sliced lights. One sliced light of a plurality of sliced light or channel may be coupled to each branch. The sliced light in each channel may be detected by a detector 114. Each branch may include one first resonator 106 and one detector 114.

Various embodiments have advantages over systems which only allow for single channel sensing. Advantageously, various embodiments having multiple channels allow for multi-channel sensing and/or wavelength demultiplexing (WDM) sensing. Various embodiments allow for multi-channel sensing and/or wavelength demultiplexing (WDM) sensing with only a single light source. WDM sensing with a single broadband light source eliminates multiple lasers with different wavelengths for each channel, thus reducing costs. Additionally, various embodiments with multiple first resonators but fewer second resonators (e.g. one second resonator) allow for multi-channel sensing but at the same time reduce power consumption.

In various embodiments, the optical sensing system 102 may further include one or more further first resonators such that the optical sensing system 102 includes a plurality of first resonators 106. The plurality of first resonators 106 may be coupled to the light separation element 104 such that each first resonator 106 of the plurality of first resonators 106 is configured to receive one respective sliced light of the plurality of sliced lights. An effective refractive index of each first resonator 106 may be changeable in response to a change in a refractive index of a cladding of the respective first resonator 106.

The optical sensing system 102 may further include a plurality of channel waveguides. Each first resonator of the plurality of first resonators 106 may be coupled to one respective channel waveguide of the plurality of channel waveguides. The respective channel waveguide may be configured to couple the respective sliced light between the light separation element 104 and the respective first resonator 106.

The optical sensing system 102 may include one or more further detectors such that the optical sensing system includes a plurality of detectors 114. One respective detector of the plurality of detectors may be configured to measure a respective intensity of the respective sliced light. The optical sensing system 102 may also include a plurality of output waveguides. One respective output waveguide of the plurality of output waveguides may be coupled to each first resonator 106. The respective output waveguide may be configured to carry the respective sliced light from each first resonator 106. The respective detector 114 may be coupled to the respective output waveguide. The respective detector 114 may be configured to receive the respective sliced light from the respective output waveguide.

In various embodiments, the respective intensity of the respective sliced light may be based on a respective difference between a respective resonant wavelength of each first resonator 106 and the resonant wavelength of the second resonator 108. The respective difference between a respective resonant wavelength of each first resonator 106 and the resonant wavelength of the second resonator 108 may be based on a respective effective refractive index of the respective first resonator 106. In various embodiments, the respective difference (between the respective resonant wavelength of each first resonator 106 and the respective resonant wavelength of the respective second resonator 108) may be based on the respective resonant wavelength of the first resonator 106 and the respective resonant wavelength of the second resonator 108. The respective resonant wavelength of the first resonator 106 may be based on the respective effective refractive index of the respective first resonator 106. In other words, the respective resonant wavelength of the first resonator 106 (and hence the effective refractive index of each first resonator 106) may be obtained based on the respective difference (from respective intensity of the respective sliced light) and the resonant wavelength of the second resonator 108.

The respective effective refractive index of each first resonator 106 may be changeable in response to a change in a respective refractive index of a respective cladding of each first resonator 106.

In various embodiments, the optical sensing system 102 may further include a coupling waveguide coupling the second resonator 108 and the light separation element 104.

In various embodiments, the optical sensing system 102 may further include an optical broadband source. The optical sensing system 102 may also include an input waveguide coupling the optical broadband source to the second resonator 108.

In various embodiments, one detector of the plurality of detectors 114 may be contacted with a reference sample. One or more of the remaining detectors of the plurality of detectors 114 may be contacted with one or more test samples. A first test sample may be the same or may be different from a second test sample.

Alternatively, in various embodiments, the optical sensing system 102 may further include one or more further second resonators such that the optical sensing system 102 includes a plurality of second resonators 108. In various embodiments, the plurality of second resonators 108 may be coupled to the light separation element 104 such that each second resonator of the plurality of second resonators 108 is configured to receive one respective sliced light of the plurality of sliced lights. The optical system 102 may further include a plurality of channel waveguides. Each second resonator may be coupled to one channel waveguide of the plurality of channel waveguides. One channel waveguide of the plurality of waveguides may be configured to couple the respective sliced light between the light separation element 104 and each second resonator 108.

In various embodiments, the optical sensing system 102 may also include one or more further first resonators such that the optical sensing system includes a plurality of first resonators 106. One respective first resonator of the plurality of first resonators 106 may be coupled to each second resonator such that the respective first resonator 106 receives the respective sliced light from each second resonator 108.

The optical sensing system 102 may also include a plurality of coupling waveguides. One respective coupling waveguide of the plurality of coupling waveguides may couple between each second resonator 108 and the respective first resonator 106. The respective coupling waveguide may be configured to carry the respective sliced light from each second resonator 108 to the respective first resonator 106.

The optical sensing system 102 may also include one or more further detectors such that the optical sensing system includes a plurality of detectors 114. One respective detector of the plurality of detectors 114 is configured to measure a respective intensity of the respective sliced light. In various embodiments, the optical sensing system 102 may include a plurality of output waveguides. One respective output waveguide of the plurality of output waveguides may be coupled to the respective first resonator 106. The respective output waveguide may be configured to carry the respective sliced light from the respective first resonator 106. The respective detector 114 may be coupled to the respective output waveguide. The respective detector 114 may be configured to receive the respective sliced light from the respective output waveguide.

The positions of the first resonators and the second resonators may be interchangeable. In other words, in various alternate embodiments, the plurality of first resonator 106 may instead by coupled to the light separation element 104 such that each first resonator of the plurality of first resonators 106 may be configured to receive one respective sliced optical light of the plurality of sliced optical light. Each first resonator 106 may be coupled to one respective channel waveguide. One respective channel waveguide maybe configured to couple the respective sliced light between the light separation element 104 and each first resonator 106. One second resonator of a plurality of second resonators 108 may be coupled to each first resonator of the plurality of first resonators 106. The respective second resonator 108 may be configured to receive the respective sliced light of the plurality of sliced lights from each first resonator 106. One respective coupling waveguide of the plurality of coupling waveguides may couple between each first resonator 106 and the respective second resonator 108. The respective coupling waveguide may be configured to carry the respective sliced light from each first resonator 106 to the respective second resonator 108. One respective output waveguide of the plurality of output waveguides may be coupled to the respective second resonator 108. The respective output waveguide may be configured to carry the respective sliced light from the respective second resonator 108. One respective detector of the plurality of detectors 114 may be coupled to the respective output waveguide. The respective detector 114 may be configured to receive the respective sliced light from the respective output waveguide.

In both cases, in various embodiments, the respective intensity of the respective sliced light may be based on a respective difference between a resonant wavelength of the respective first resonator and a respective resonant wavelength of each second resonator. The respective difference between the respective resonant wavelength of the respective first resonator and the respective resonant wavelength of each second resonator may be based on a respective effective refractive index of the respective first resonator. The respective difference between the respective resonant wavelength of the respective first resonator and the respective resonant wavelength of each second resonator may be based on the respective resonant wavelength of the respective first resonator and the respective resonant wavelength of each second resonator. The respective resonant wavelength of the respective first resonator may be based on a respective effective refractive index of the respective first resonator.

The respective effective refractive index of the respective first resonator may be changeable in response to a change in a respective refractive index of a respective cladding of the respective first resonator.

In various embodiments, the optical sensing system may include an optical broadband source. The optical sensing system 102 may further include an input waveguide coupling the optical broadband source to the light separation element 104.

Generally speaking, the waveguides serve to couple light between the other optical elements such as detectors, resonators, source and light separation element. A person skilled in the art would appreciate that in light may also be coupled directly between the optical elements in appropriate situations.

The cladding of the first resonator 106 may include or may be an oxide cladding, for example $SiO_2$ or InAlAs oxide (InAlAs($O_x$)). The cladding may be formed using a complementary metal oxide semiconductor (CMOS) compatible fabrication process, for providing a cost effective optical sensing system.

In various embodiments, the detector 114 may include photodetectors such as photodiodes or charge-coupled devices (CCDs). In various embodiments, the detector may be one detector of an integrated photodetector array. Electrical read-out may be done via the photodetector array for sensing interrogation. An integrated photodetector array may result in compact device footprint and/or lower fabrication costs compared to off-the-shelf photodetectors.

Figure 2A:
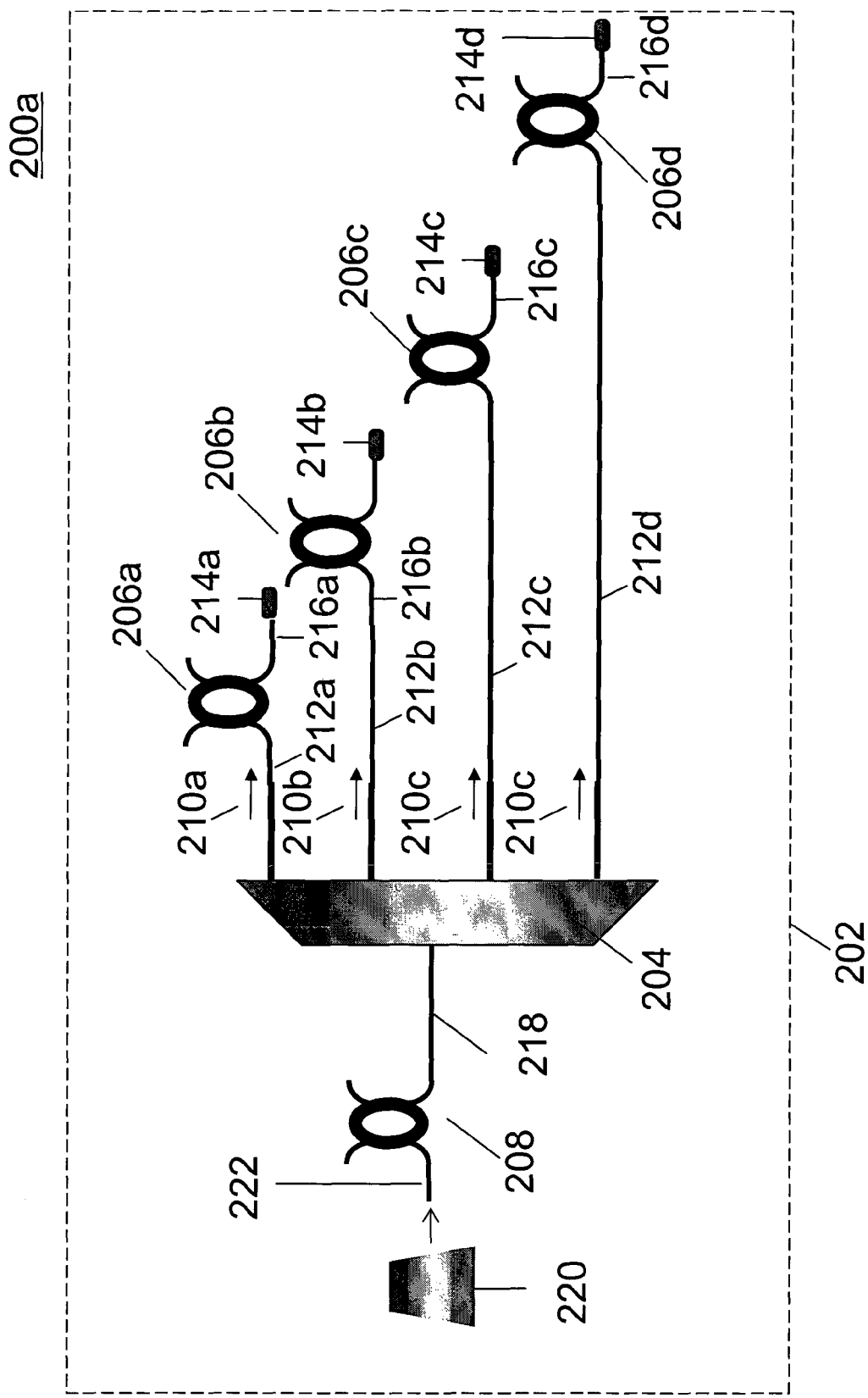
FIG. 2A is a schematic showing an optical sensing system according to various embodiments.

FIG. 2A is a schematic 200a showing an optical sensing system 202 according to various embodiments. The optical sensing system 202 may include a light separation element 204 configured to separate an input light into a plurality of sliced lights. The optical sensing system 202 may further include a first resonator 206a configured to receive one sliced light 210a of the plurality of sliced lights 210a, 210b, 210c, 210d, wherein an effective refractive index of the first resonator 206a is changeable in response to a change in a refractive index of a cladding of the first resonator 206a. In addition, the optical sensing system 202 may include a second resonator 208 coupled to the first resonator 206a. The optical sensing system 202 may further include a detector 214a configured to measure an intensity of the sliced light 210a. The intensity of the sliced light 210a may be based on a difference between a resonant wavelength of the first resonator 106 and a resonant wavelength of the second resonator 108. The difference between the resonant wavelength of the first resonator 206a and the resonant wavelength of the second resonator 208 may be based on an effective refractive index of the first resonator 206a.

In various embodiments, the difference between the resonant wavelength of the first resonator 206a and the resonant wavelength of the second resonator 208 may be based on the resonant wavelength of the first resonator 206a and the resonant wavelength of the second resonator 208. The resonant wavelength of the first resonator 206a may be based on the effective refractive index of the first resonator 206a.

In various embodiments, the resonant wavelength of the second resonator 208 may be adjustable to a current or voltage applied to the second resonator 208.

In various embodiments, the optical sensing system 202 may further include one or more further first resonators 206b, 206c, 206d such that the optical sensing system 202 includes a plurality of first resonators 206a, 206b, 206c, 206d. The plurality of first resonators 206a, 206b, 206c, 206d may be coupled to the light separation element 204 such that each first resonator of the plurality of first resonators 206a, 206b, 206c, 206d is configured to receive one respective sliced light of the plurality of sliced lights 210a, 210b, 210c, 210d. An effective refractive index of each first resonator may be changeable in response to a change in a refractive index of a cladding of the respective first resonator. For instance, as shown in FIG. 2A, the first resonator 206a may be configured to receive sliced light 210a, the first resonator 206b may be configured to receive sliced light 210b, the first resonator 206c may be configured to receive sliced light 210c and the first resonator 206d may be configured to receive sliced light 210d.

The optical sensing system 202 may further include a plurality of channel waveguides 212a, 212b, 212c, 212d. Each first resonator of the plurality of first resonators 206a, 206b, 206c, 206d may be coupled to one respective channel waveguide of the plurality of channel waveguides 212a, 212b, 212c, 212d. For instance, as shown in FIG. 2A, the first resonator 206a may be coupled to the channel waveguide 212a, the first resonator 206b may be coupled to the channel waveguide 212b, the first resonator 206c may be coupled to the channel waveguide 212c and the first resonator 206d may be coupled to the channel waveguide 212d.

The respective channel waveguide may be configured to couple the respective sliced light between the light separation element 204 and the respective first resonator. For instance, the channel waveguide 212a may be configured to couple the sliced light 210a between the light separation element 204 and the first resonator 206a, the channel waveguide 212b may be configured to couple the sliced light 210b between the light separation element 204 and the first resonator 206b, the channel waveguide 212c may be configured to couple the sliced light 210c between the light separation element 204 and the first resonator 206c and the channel waveguide 212d may be configured to couple the sliced light 210d between the light separation element 204 and the first resonator 206d. The respective channel waveguide may be configured to couple the sliced light between the light separation element 204 and a respective 'input' port of the respective first resonator. As the respective sliced light goes through each first resonator, a portion of the respective sliced light may be lost through a respective 'through' port of each resonator. The remaining portion of the respective sliced light may be outputted to a respective 'drop' port of each first resonator.

The optical sensing system 202 may include one or more further detectors 214b, 214c, 214d such that the optical sensing system 202 includes a plurality of detectors 214a, 214b, 214c, 214d. One respective detector of the plurality of detectors 214a, 214b, 214c, 214d may be configured to measure a respective intensity of the respective sliced light. Detector 214a may be configured to measure an intensity of sliced light 210a, detector 214b may be configured to measure an intensity of sliced light 210b, detector 214c may be configured to measure an intensity of sliced light 210c and detector 214d may be configured to measure an intensity of sliced light 210d. The respective sliced light measured by the respective detector may be the remaining portion of the respective sliced light outputted from the respective 'drop' of each first resonator. In various embodiments, the plurality of detectors may be an integrated photodetector array. Electrical read-out may be done via the photodetector array for sensing interrogation. An integrated photodetector array may result in compact device footprint and/or lower fabrication costs compared to off-the-shelf photodetectors.

The optical sensing system 202 may also include a plurality of output waveguides 216a, 216b, 216c, 216d. One respective output waveguide of the plurality of output waveguides 216a, 216b, 216c, 216d may be coupled to each first resonator. For instance, output waveguide 216a may be coupled to first resonator 206a, output waveguide 216b may be coupled to first resonator 206b, output waveguide 216c may be coupled to first resonator 206c and output waveguide 216d may be coupled to first resonator 206d. The respective output waveguide may be coupled to the respective 'drop' port of each first resonator.

The respective output waveguide may be configured to carry the respective sliced light from each first resonator. Output waveguide 216a may be configured to carry sliced light 210a from first resonator 206a, output waveguide 216b may be configured to carry sliced light 210b from first resonator 206b, output waveguide 216c may be configured to carry sliced light 210c from first resonator 206c and output waveguide 216d may be configured to sliced light 210d from first resonator 206d.

The respective detector may be coupled to the respective output waveguide. Detector 214a may be coupled to output waveguide 216a, detector 214b may be coupled to output waveguide 216b, detector 214c may be coupled to output waveguide 216c and detector 214d may be coupled to output waveguide 216d. The respective detector may be configured to receive the respective sliced light from the respective output waveguide. Detector 214a may be configured to receive the sliced light 210a from the output waveguide 216a, detector 214b may be configured to receive the sliced light 210b from the output waveguide 216b, detector 214c may be configured to receive the sliced light 210c from the output waveguide 216c and detector 214d may be configured to receive the sliced light 210d from the output waveguide 216d.

In various other embodiments, the respective detector of the plurality of detectors 214a, 214b, 214c, 214d may be coupled directly to each first resonator of the plurality of resonators 206a, 206b, 206c, 206d. The respective detector may be configured to receive the respective sliced light from the respective resonator.

In various embodiments, the respective detector may be configured to measure an intensity of the respective sliced light received from the respective output waveguide. Detector 214a may be configured to measure an intensity of sliced light 210a received from output waveguide 216a, detector 214b may be configured to measure an intensity of sliced light 210b received from output waveguide 216b, detector 214c may be configured to measure an intensity of sliced light 210c received from output waveguide 216c and detector 214d may be configured to measure an intensity of sliced light 210d received from output waveguide 216d.

In various embodiments, the respective intensity of the respective sliced light may be based on a respective difference between a respective resonant wavelength of each first resonator and the resonant wavelength of the second resonator. For instance, the intensity of sliced light 210a may be based on a difference between a resonant wavelength of first resonator 206a and the resonant wavelength of the second resonator 208, the intensity of sliced light 210b may be based on a difference between a resonant wavelength of first resonator 206b and the resonant wavelength of the second resonator 208, the intensity of sliced light 210c may be based on a difference between a resonant wavelength of first resonator 206c and the resonant wavelength of the second resonator 208 and the intensity of sliced light 210d may be based on a difference between a resonant wavelength of first resonator 206d and the resonant wavelength of the second resonator 208.

The respective difference between the respective resonant wavelength of each first resonator and the resonant wavelength of the second resonator 208 may be based on a respective effective refractive index of the respective first resonator. In various embodiments, the respective difference (between the respective resonant wavelength of each first resonator and the respective resonant wavelength of the respective second resonator 208) may be based on the respective resonant wavelength of the first resonator and the respective resonant wavelength of the second resonator 208. The respective resonant wavelength of the first resonator may be based on the respective effective refractive index of the respective first resonator. In other words, the respective resonant wavelength of the first resonator (and hence the effective refractive index of each first resonator) may be obtained based on the respective difference (from respective intensity of the respective sliced light) and the resonant wavelength of the second resonator 208.

In various embodiments, the intensity of the respective sliced light may be maximum when an optical resonant wavelength (or optical resonant frequency) of the respective first resonator and an optical resonant wavelength (or optical resonant frequency) of the second resonator 208 are aligned. The intensity of the sliced light 210a may be maximum when an optical resonant wavelength of the first resonator 206a and an optical resonant wavelength of the second resonator 208 are aligned, the intensity of the sliced light 210b may be maximum when an optical resonant wavelength of the first resonator 206b and the optical resonator wavelength of the second resonator 208 are aligned, the intensity of the sliced light 210c may be maximum when an optical resonant wavelength of the first resonator 206c and the optical resonant wavelength of the second resonator 208 are aligned, and the intensity of the sliced light 210d may be maximum when an optical resonant wavelength of the first resonator 206d and an optical resonant wavelength of the second resonator 208 are aligned.

The optical resonant wavelength (or optical resonant frequency) of the respective first resonator may change in response to the change in the effective refractive index of the respective first resonator. For instance, the optical resonant wavelength of the first resonator 206a may change in response to the change in the effective refractive index of the first resonator 206a, the optical resonant wavelength of the first resonator 206b may change in response to the change in the effective refractive index of the first resonator 206b, optical resonant wavelength of the first resonator 206c may change in response to the change in the effective refractive index of the first resonator 206c and optical resonant wavelength of the first resonator 206d may change in response to the change in the effective refractive index of the first resonator 206d.

In various embodiments, the optical sensing system 202 may further include a coupling waveguide 218 coupling the second resonator 208 and the light separation element 204. The respective index of each first resonator may be changeable in response to a change in a respective refractive index of a respective cladding of each first resonator.

In various embodiments, the optical sensing system 202 may further include an optical broadband source 220. The optical sensing system 102 may also include an input waveguide 222 coupling the optical broadband source 220 to the second resonator 208. The optical broadband source 220 may instead be coupled directly to the second resonator 208. In various embodiments, the broadband source 220 may be an amplified spontaneous emission (ASE) light source, a super-luminescent diode. Various embodiments may lower costs compared to using a high resolution tunable laser or multiple single wavelength lasers.

In various embodiments, light from the optical broadband source 220 may be coupled either directly or via input waveguide 222 to the second resonator 208. A portion of the light may be outputted to a through port of the second resonator. Another portion of the light may be coupled to the second resonator 208, which may propagate and cycle through and within the second resonator 208, where part of the light may be dropped and coupled to the light separation element 204 either directly or through coupling waveguide 218. The light coupled to the light separation element 204 may be dispersed according to the wavelength. For instance, light having a first range of wavelengths (i.e. sliced light 210a) may be coupled to the first resonator 206a directly or via coupling waveguide 212a. Light having a second range of wavelengths (i.e. sliced light 210b) may be coupled to the first resonator 206b directly or via coupling waveguide 212b. Light having a third range of wavelength (i.e. sliced light 210c) may be coupled to the first resonator 206c directly or via coupling waveguide 212c and light having a third range of wavelength (i.e. sliced light 210d) may be coupled to the first resonator 206d directly or via coupling waveguide 212d.

A portion of the sliced light 210a may pass through the first resonator 206a and be outputted through a through port of the first resonator 206a. Another portion of the sliced light 210a may be coupled to the first resonator 206a, which may propagate and cycle through and within the first resonator 206a, where part of the sliced light 210a may be dropped and coupled to the detector 214a, either directly or through the output waveguide 216a.

Similarly, a portion of the sliced light 210b may pass through the first resonator 206b and be outputted through a through port of the first resonator 206b. Another portion of the sliced light 210b may be coupled to the first resonator 206b, which may propagate and cycle through and within the first resonator 206b, where part of the sliced light 210b may be dropped and coupled to the detector 214b, either directly or through the output waveguide 216b.

Likewise, a portion of the sliced light 210c may pass through the first resonator 206c and be outputted through a through port of the first resonator 206c. Another portion of the sliced light 210c may be coupled to the first resonator 206c, which may propagate and cycle through and within the first resonator 206c, where part of the sliced light 210c may be dropped and coupled to the detector 214c, either directly or through the output waveguide 216c.

Also, a portion of the sliced light 210d may pass through the first resonator 206d and be outputted through a through port of the first resonator 206d. Another portion of the sliced light 210d may be coupled to the first resonator 206d, which may propagate and cycle through and within the first resonator 206d, where part of the sliced light 210d may be dropped and coupled to the detector 214d, either directly or through the output waveguide 216d.

Figure 2B:
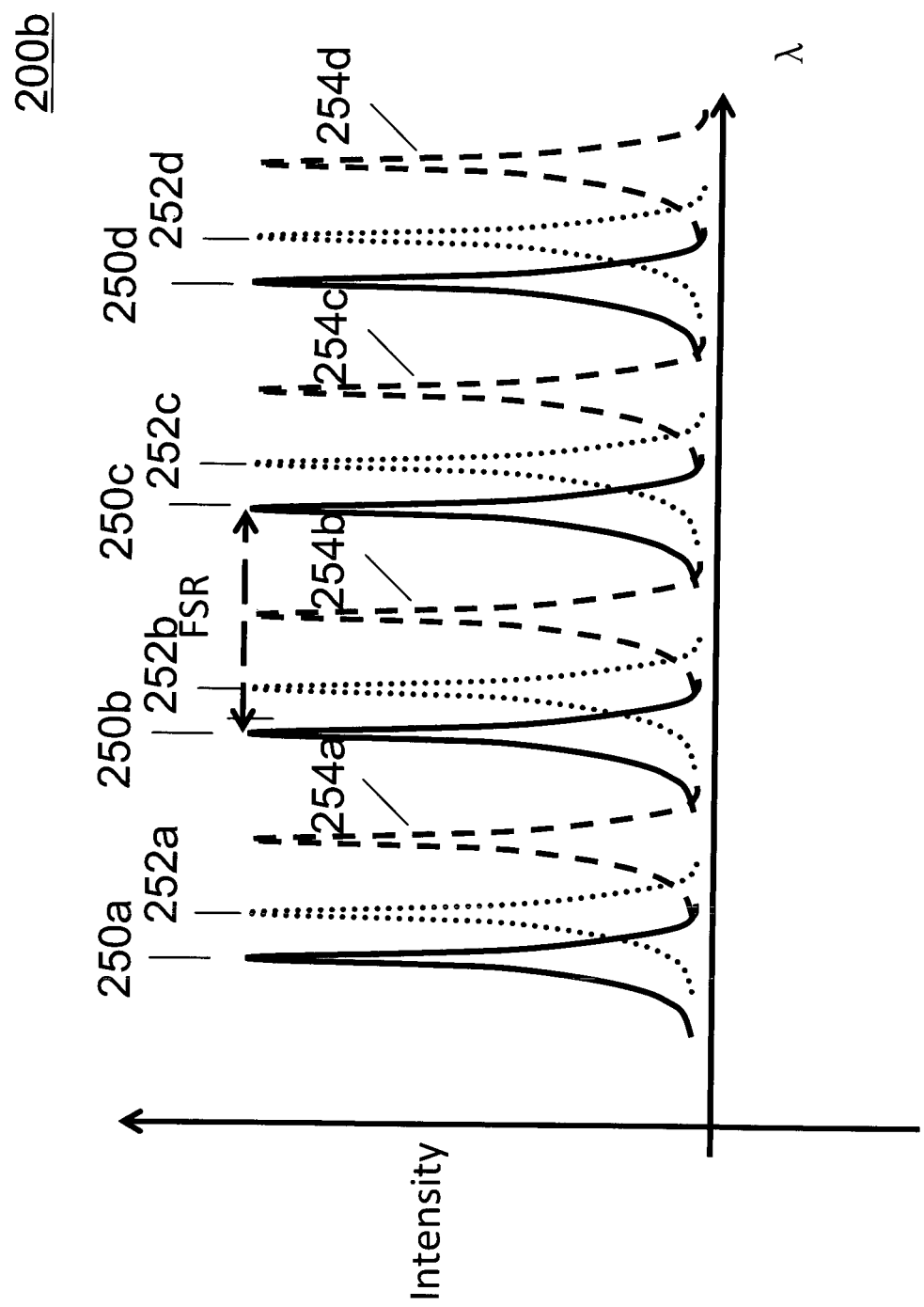
FIG. 2B is a graph of intensity against wavelength (λ) of input light outputted by a tracing element (e.g. second resonator) according to various embodiments.

FIG. 2B is a graph 200b of intensity against wavelength ($\lambda$) of input light outputted by a tracing element (e.g. second resonator 208) according to various embodiments. As shown in FIG. 2B, light outputted by the second resonator 208 may have multiple resonant wavelengths shown by the plurality of peaks 250a, 250b, 250c, 250d. As the second resonator 208 is adjusted (e.g. by a current or voltage applied to the second resonator 208), the multiple resonant wavelengths may shift by the same amount. For instance, peak 250a may be shifted by an amount to peak 252a. Peak 250b may be shifted by the same amount to 252b. Similarly, peak 250c may be shifted by the same amount to 252c and peak 250d may be shifted by the same amount to 252d. As the second resonator 208 is further adjusted, peak 252a may be shifted by a further amount to 254a, peak 252b may be shifted by the same further amount to 254b, peak 252c may be shifted by the same further amount to 254c and peak 252d may be shifted by the same further amount to 254d. The difference between successive resonant wavelengths may be termed as free spectral range (FSR).

Figure 2C:
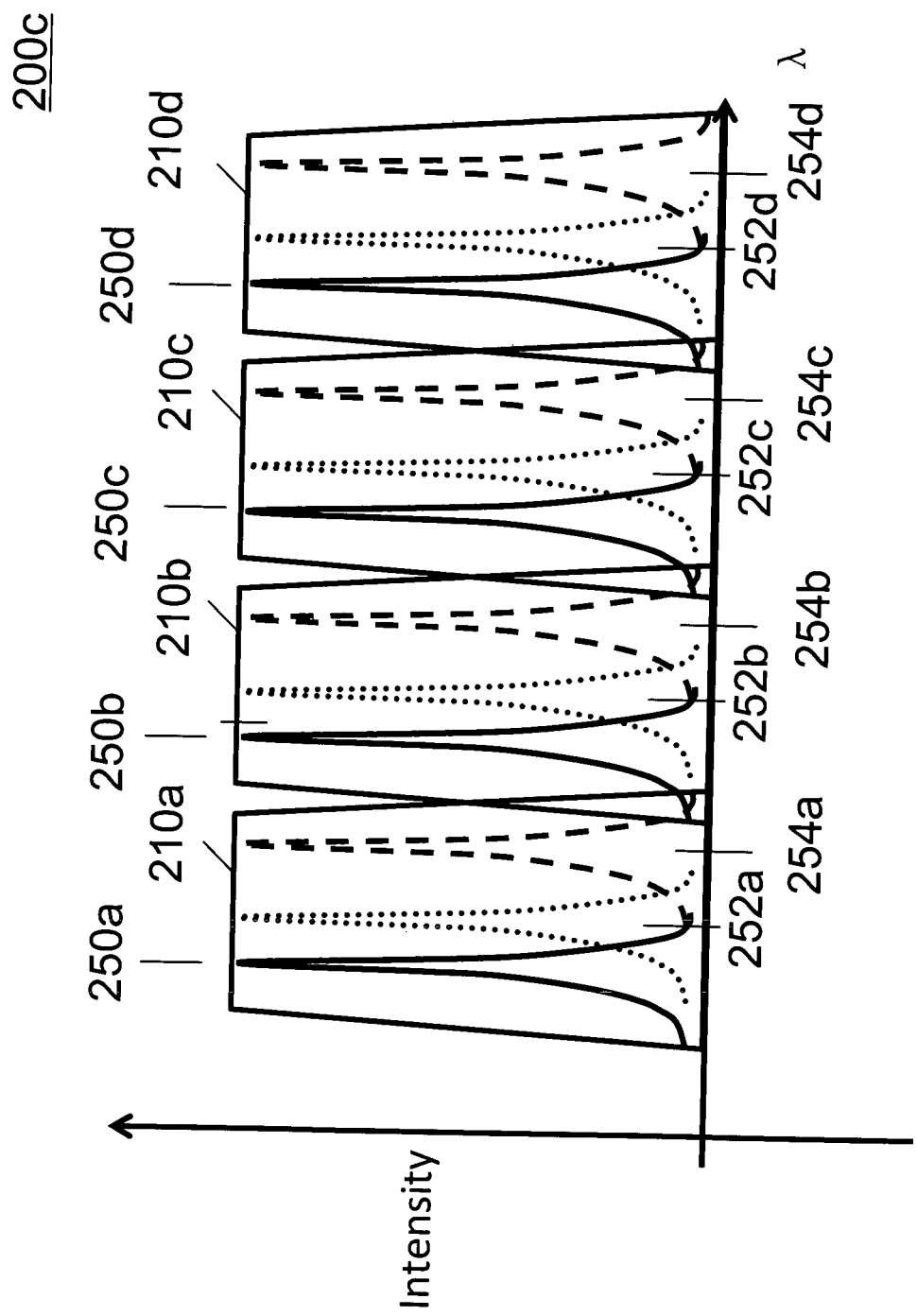
FIG. 2C is a graph of intensity against wavelength (λ) illustrating the separation of the input light into a plurality of sliced lights according to various embodiments.

FIG. 2C is a graph 200c of intensity against wavelength ($\lambda$) illustrating the separation of the input light into a plurality of sliced lights 210a, 210b, 210c, 210d according to various embodiments. The input light shown in FIG. 2B may be separated into different channels (i.e. a plurality of sliced lights 210a, 210b, 210c, 210d). The light separation element 204 may be configured such that the bandwidth (i.e. range of wavelengths) of each sliced light is substantially equal to the FSR.

Figure 2D:
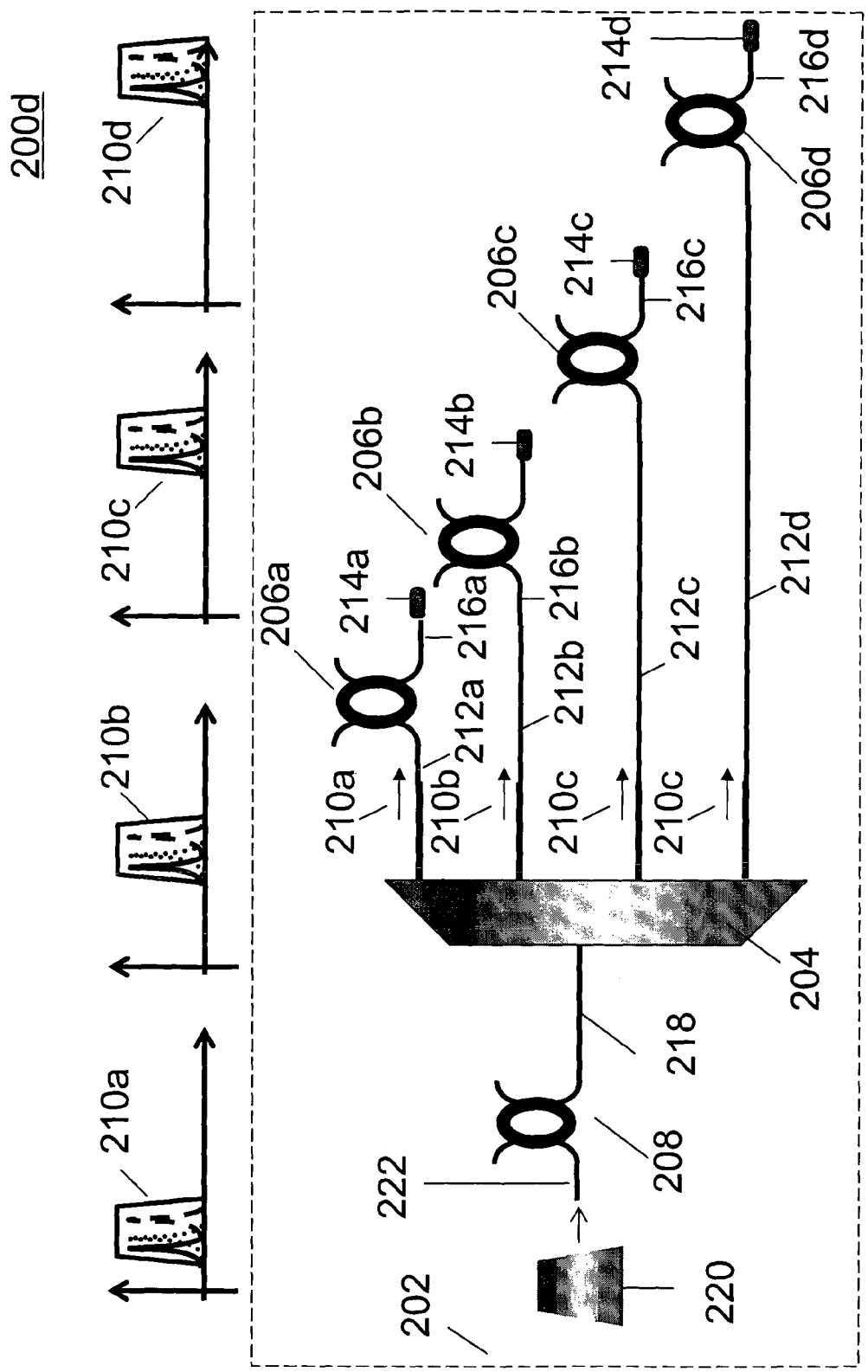
FIG. 2D is a schematic illustrating the spectra of each sliced light of the plurality of sliced light going down the respective branch of the optical sensing system shown in FIG. 2A according to various embodiments.

FIG. 2D is a schematic 200d illustrating the spectra of each sliced light of the plurality of sliced light going down the respective branch of the optical sensing system 202 shown in FIG. 2A according to various embodiments.

Figure 2E:
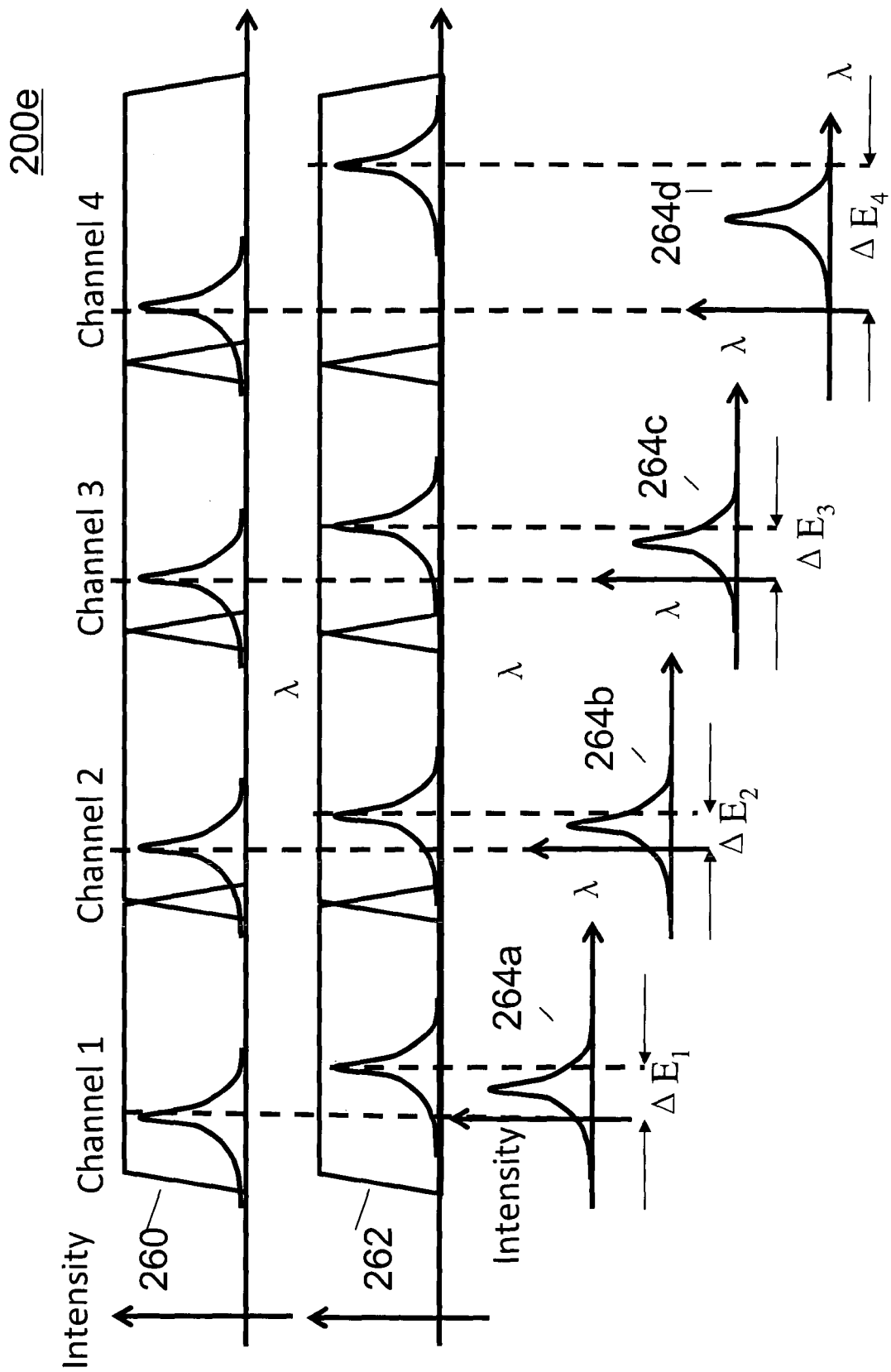
FIG. 2E is a schematic illustrating the relationship of the resonant wavelength of the second resonator, the first resonant wavelength of each first resonator as well as the resultant respective intensity of the respective sliced optical light.

FIG. 2E is a schematic 200e illustrating the relationship of the resonant wavelength of the second resonator, the first resonant wavelength of each first resonator as well as the resultant respective intensity of the respective sliced optical light. Each first resonator or sensing element may be configured to have the same FSR as the second resonator. Graph 260 is a plot of intensity against wavelength of the input light similar to the graph shown in FIG. 2B when a particular current or voltage is applied to the second resonator 208. Graph 262 is a plot of intensity against wavelength of the respective sliced light outputted from each first resonator. Each first resonator is in contact with a different sample. As a result, the effective refractive index of each first resonator changes by different amounts. The respective resonant wavelength of each first resonator is shifted by a different amount. On the other hand, the second resonator 208 may be configured to shift each of the multiple resonant wavelengths of the light outputted by the second resonator 208 by the same amount when the voltage or current applied to the second resonator 208 is adjusted. Graphs 264a, 264b, 264c, 264d are the respective intensity of the respective sliced light measured at the respective detector.

The respective intensity of the respective sliced light measured at the respective detector may be different as the respective separation (between the resonant wavelength of the second resonator 208 and the respective wavelengths of the respective resonator) is different (due to each first resonator placed in contact with a different sample).

For instance, ΔE1 (separation of the resonant wavelength of the second resonator 208 and the resonant wavelength of the first resonator 206a) may be different from ΔE2 (separation of the resonant wavelength of the second resonator 208 and the resonant wavelength of the first resonator 206b). As such, the peak intensity of the sliced light 210a in graph 264a may be different from the peak intensity of the sliced light 210b in graph 264b. Similarly, ΔE3 (separation of the resonant wavelength of the second resonator 208 and the resonant wavelength of the first resonator 206c) may be different from ΔE1/ΔE2. As such, the peak intensity of the sliced light 210c in graph 264c may be different from the peak intensities in graph 264a/264b. Also, ΔE4 (separation of the resonant wavelength of the second resonator 208 and the resonant wavelength of the first resonator 206d) may be different from ΔE1/ΔE2/ΔE3. As such, the peak intensity of the sliced light 210d in graph 264d may be different from the peak intensities in graph 264a/264b/264c. In various embodiments, the difference or separation of the resonant wavelength of the second resonator and the resonant wavelength of each first resonator (ΔE) may be determined from respective intensity of the respective sliced light. In various embodiments, ΔE may be proportional to the intensity of the sliced light measured.

The sliced light 210a coupled to the first resonator 206a may include a wavelength equal to or near an initial resonant wavelength of the first resonator 206a. The initial resonant wavelength of the first resonator 206a may be $\lambda_s$ and the resonant wavelength of the second resonator 208 may be $\lambda_r$. $\lambda_s$ may be at or near $\lambda_r$. When the first resonator 206b comes into contact with a biological or chemical sample, the resonant wavelength of the first resonator 206a may shift, i.e. from $\lambda_s$ to $\lambda_{s'}$. The intensity of sliced light 210 coupled from the drop port of the first resonator 206a to the detector 214a (either directly or through an output waveguide 216a) may thus decrease as a result of the increased misalignment in optical resonances of the first resonator 206a and the second resonator 208. In other words, the intensity of sliced light 210a may decrease because $\lambda_{s'}$ may not be at or near $\lambda_r$. In order to increase or maximize the intensity of the sliced light 210a, the second resonator 208 may be tuned via electro-optic or thermo-optic effect to shift the resonant wavelength of the second resonator such that the shifted resonant wavelength $\lambda_{r'}$ of the second resonator again coincides with or is near the shifted resonant wavelength $\lambda_{s'}$ of the first resonator 206a.

In various embodiments, adjusting the second resonator 208 may shift the resonant wavelength of the second resonator 208 in each branch by the same amount. In various embodiments, a voltage or current may be applied such that the respective intensities measured at more than one respective detectors or all the detectors are more than zero. In other words, it may be possible to adjust the current or voltage applied to the second resonator 208 such that peaks are detected by more than one detector or all the detectors. Various embodiments allow for sensing by more than one first resonators or all the first resonators at the same time. Various embodiments allow simultaneous sensing of multiple samples. Various embodiments allow for sensing by more than one first resonators or all the first resonators at the same time using one second resonator 208.

Various embodiments may use wavelength demultiplexing (WDM) sensing using multiple sensing microrings with few tracing (e.g. one) tracing microring. Various embodiments may eliminate multiple lasers with different wavelengths for each channel by using a broadband light source and using WDM sensing.

Figure 3:
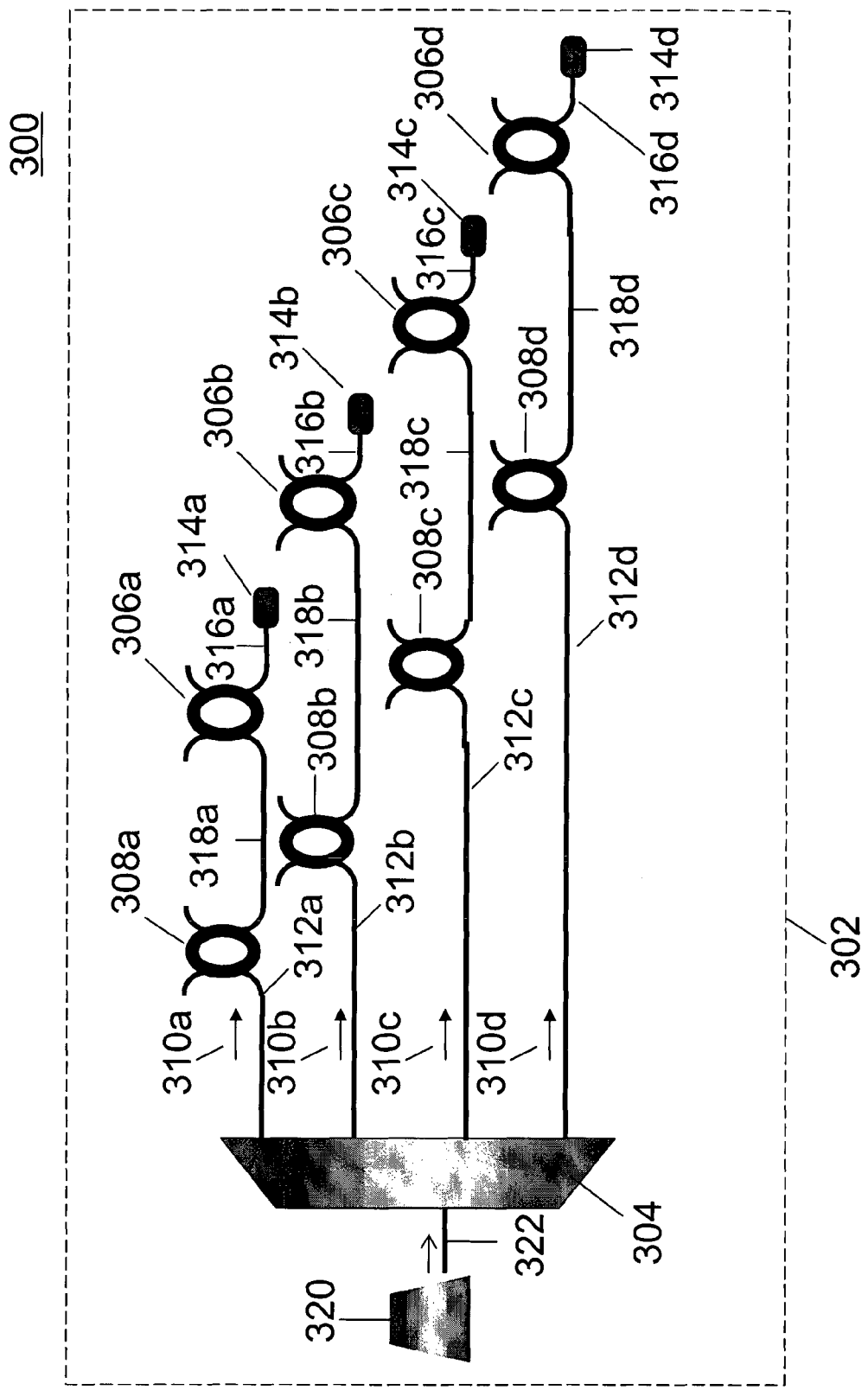
FIG. 3 is a schematic showing an optical sensing system according to various embodiments.

FIG. 3 is a schematic 300 showing an optical sensing system 302 according to various embodiments. The optical sensing system 302 may include a light separation element 304 configured to separate an input light into a plurality of sliced lights. The optical sensing system 302 may further include a first resonator 306a configured to receive one sliced light 310a of the plurality of sliced lights 310a, 310b, 310c, 310d. An effective refractive index of the first resonator 306a may be changeable in response to, a change in a refractive index of a cladding of the first resonator 306a. In addition, the optical sensing system 302 may include a second resonator 308 coupled to the second resonator 308. The optical sensing system 302 may further include a detector 314a configured to measure an intensity of the sliced light 310a. The intensity of the sliced light 310a may be based on a difference between a resonant wavelength of the first resonator 306a and a resonant wavelength of the second resonator 308. The difference between a resonant wavelength of the first resonator 306a and a resonant wavelength of the second resonator 308 may be based on the effective refractive index of the first resonator 306a.

In various embodiments, the difference between the resonant wavelength of the first resonator 306a and the resonant wavelength of the second resonator 308 may be based on the resonant wavelength of the first resonator 306a and the resonant wavelength of the second resonator 308. The resonant wavelength of the first resonator 306a may be based on the effective refractive index of the first resonator 306a.

In various embodiments, the resonant wavelength of the second resonator 308 may be adjustable to a current or voltage applied to the second resonator 308.

The optical sensing system 302 may further include one or more further second resonators 308b, 308c, 308d such that the optical sensing system 302 includes a plurality of second resonators 308a, 308b, 308c, 308d. The plurality of second resonators 308a, 308b, 308c, 308d may be coupled to the light separation element 304 such that each second resonator of the plurality of second resonators 308a, 308b, 308c, 308d may be configured to receive one respective sliced light of the plurality of sliced light 310a, 310b, 310c, 310d. For instance, second resonator 308a may be coupled to the light separation element 304 such that the second resonator 308a may be configured to receive sliced light 310a, second resonator 308b may be coupled to the light separation element 304 such that the second resonator 308b may be configured to receive sliced light 310b, second resonator 308c may be coupled to the light separation element 304 such that the second resonator 308c may be configured to receive sliced light 310c and second resonator 308d may be coupled to the light separation element 304 such that the second resonator 308d may be configured to receive sliced light 310d.

The optical sensing system 302 may further include a plurality of channel waveguides 312a, 312b, 312c, 312d. One channel waveguide of the plurality of waveguides may be coupled to each second resonator of the plurality of second resonators 308a, 308b, 308c, 308d. Channel waveguide 312a may be coupled to second resonator 308a, channel waveguide 312b may be coupled to the second resonator 308b, channel waveguide 312c may be coupled to the second resonator 308c and channel waveguide 312d may be coupled to the second resonator 308d. One channel waveguide may be configured to couple a respective sliced light from the wavelength separation element 304 to each second resonator. For instance, channel waveguide 312a may be configured to coupled sliced light 310a from the wavelength separation element 304 to second resonator 308a, channel waveguide 312b may be configured to coupled sliced light 310b from the wavelength separation element 304 to second resonator 308b, channel waveguide 312c may be configured to coupled sliced light 310c from the wavelength separation element 304 to second resonator 308c and channel waveguide 312d may be configured to coupled sliced light 310d from the wavelength separation element 304 to second resonator 308d.

In various embodiments, the optical sensing system 302 may also include one or more further first resonators 306b, 306c, 306d such that the optical sensing system 302 includes a plurality of first resonators 306a, 306b, 306c, 306d. One respective first resonator of the plurality of first resonators 306a, 306b, 306c, 306d may be coupled to each second resonator such that the respective first resonator receives the respective sliced light from each second resonator. For instance, first resonator 306a may be coupled to second resonator 308a such that the first resonator 306a receives sliced light 310a from second resonator 308a, first resonator 306b may be coupled to second resonator 308b such that the first resonator 306b receives sliced light 310b from second resonator 308b, first resonator 306c may be coupled to second resonator 308c such that the first resonator 306c receives sliced light 310c from second resonator 308c and first resonator 306d may be coupled to second resonator 308d such that the first resonator 306d receives sliced light 310d from second resonator 308d.

The optical sensing system 302 may also include a plurality of coupling waveguides 318a, 318b, 318c, 318d. One respective coupling waveguide of the plurality of coupling waveguides 318a, 318b, 318c, 318d may couple between each second resonator and the respective first resonator. Coupling waveguide 318a may couple between second resonator 308a and first resonator 306a, coupling waveguide 318b may couple between second resonator 308b and first resonator 306b, coupling waveguide 318c may couple between second resonator 308c and first resonator 306c and coupling waveguide 318d may couple between second resonator 308d and first resonator 306d. The respective coupling waveguide may be configured to carry the respective sliced light from each second resonator to the respective first resonator. Coupling waveguide 318a may be configured to carry sliced light 310a from the second resonator 308a to first resonator 306a, coupling waveguide 318b may be configured to carry sliced light 310b from the second resonator 308b to first resonator 306b, coupling waveguide 318c may be configured to carry sliced light 310c from the second resonator 308c to first resonator 306c and coupling waveguide 318d may be configured to carry sliced light 310d from the second resonator 308d to first resonator 306d.

The optical sensing system 302 may also include one or more detectors 314b, 314c, 314d such that the optical sensing system 302 include a plurality of detectors 314a, 314b, 314c, 314d. In various embodiments, the optical sensing system 302 may include a plurality of output waveguides 316a, 316b, 316c, 316d. One respective output waveguide of the plurality of output waveguides 316a, 316b, 316c, 316d may be coupled to the respective first resonator. Output waveguide 316a may be coupled to the first resonator 306a, output waveguide 316b may be coupled to the first resonator 306b, output waveguide 316c may be coupled to the first resonator 306c and output waveguide 316d may be coupled to the first resonator 306d. The respective output waveguide may be configured to carry the respective sliced light from the respective first resonator. For instance, output waveguide 316a may be configured to carry sliced light 310a from the first resonator 306a, output waveguide 316b may be configured to carry sliced light 310b from the first resonator 306b, output waveguide 316c may be configured to carry sliced light 310c from the first resonator 306c and output waveguide 316d may be configured to carry sliced light 310d from the first resonator 306d. The respective detector of the plurality of detectors may be coupled to the respective output waveguide. The respective detector may be configured to receive the respective sliced light from the respective output waveguide. Detector 314a may be configured to receive sliced light 310a from the output waveguide 316a, detector 314b may be configured to receive sliced light 310b from the output waveguide 316b, detector 314c may be configured to receive sliced light 310c from the output waveguide 316c and detector 314d may be configured to receive sliced light 310d from the output waveguide 316d.

The respective detector may be configured to measure an intensity of the respective sliced light received from the respective output waveguide. Detector 314a may be configured to measure an intensity of sliced light 310a received from output waveguide 316a, detector 314b may be configured to measure an intensity of sliced light 310b received from output waveguide 316b, detector 314c may be configured to measure an intensity of sliced light 310c received from output waveguide 316c and detector 314d may be configured to measure an intensity of sliced light 310d received from output waveguide 316d.

In various embodiments, the respective intensity of the respective sliced light may be based on a respective difference between a respective resonant wavelength of the respective first resonator and a respective resonant wavelength of each second resonator. For instance, the intensity of sliced light 310a may be based on a difference between a resonant wavelength of first resonator 306a and a resonant wavelength of second resonator 308a, the intensity of sliced light 310b may be based on a difference between a resonant wavelength of first resonator 306b and a resonant wavelength of second resonator 308b, the intensity of sliced light 310c may be based on a difference between a resonant wavelength of first resonator 306c and a resonant wavelength of second resonator 308c and the intensity of sliced light 310d may be based on a difference between a resonant wavelength of first resonator 306d and a resonant wavelength of second resonator 308d.

The respective difference between the respective resonant wavelength of the respective first resonator and the respective resonant wavelength of each second resonator may be based on a respective effective refractive index of the respective first resonator. For instance, the difference between the resonant wavelength of the first resonator 306a and the resonant wavelength of the second resonator 308a may be based on a respective effective refractive index of the first resonator 306a, the difference between the resonant wavelength of the first resonator 306b and the resonant wavelength of the second resonator 308b may be based on a respective effective refractive index of the first resonator 306b, the difference between the resonant wavelength of the first resonator 306c and the resonant wavelength of the second resonator 308c may be based on a respective effective refractive index of the first resonator 306c and the difference between the resonant wavelength of the first resonator 306d and the resonant wavelength of the second resonator 308d may be based on a respective effective refractive index of the first resonator 306d.

The respective difference between the respective resonant wavelength of the respective first resonator and the respective resonant wavelength of each second resonator may be based on the respective resonant wavelength of the respective first resonator and the respective resonant wavelength of each second resonator. The respective resonant wavelength of the respective first resonator may be based on a respective effective refractive index of the respective first resonator.

The intensity of the respective sliced light may be maximum when an optical resonant wavelength of the respective first resonator and an optical resonant wavelength of each second resonator are aligned. The intensity of sliced light 310a may be maximum when an optical resonant wavelength of the first resonator 306a and an optical resonant wavelength of the second resonator 308a are aligned, the intensity of sliced light 310b may be maximum when an optical resonant wavelength of the first resonator 306b and an optical resonant wavelength of the second resonator 308b are aligned, the intensity of sliced light 310c may be maximum when an optical resonant wavelength of the first resonator 306c and an optical resonant wavelength of the second resonator 308c are aligned and the intensity of sliced light 310d may be maximum when an optical resonant wavelength of the first resonator 306d and an optical resonant wavelength of the second resonator 308d are aligned.

An effective refractive index of each first resonator may be changeable in response to change in a refractive index of a cladding of the respective first resonator. The effective refractive index of first resonator 306a may be changeable in response to a change in a refractive index of a cladding of the first resonator 306a, the effective refractive index of first resonator 306b may be changeable in response to a change in a refractive index of a cladding of the first resonator 306b, the effective refractive index of first resonator 306c may be changeable in response to a change in a refractive index of a cladding of the first resonator 306c and the effective refractive index of first resonator 306d may be changeable in response to a change in a refractive index of a cladding of the first resonator 306d.

The resonant wavelength of the respective first resonator may change in response to the change in the effective refractive index of the respective first resonator. The resonant wavelength of the first resonator 306a may change in response to the change in the effective refractive index of the first resonator 306a, the resonant wavelength of the first resonator 306b may change in response to the change in the effective refractive index of the first resonator 306b, the resonant wavelength of the first resonator 306c may change in response to the change in the effective refractive index of the first resonator 306c and the resonant wavelength of the first resonator 306d may change in response to the change in the effective refractive index of the first resonator 306d.

In various embodiments, the optical sensing system 302 may include an optical broadband source 320. In various embodiments, the broadband source 320 may be an amplified spontaneous emission (ASE) light source or a superluminescent diode. Various embodiments may lower costs compared to using a high resolution tunable laser or multiple single wavelength lasers.

The optical sensing system 302 may further include an input waveguide 322 coupling the optical broadband source 320 to the light separation element 304.

Figure 4A:
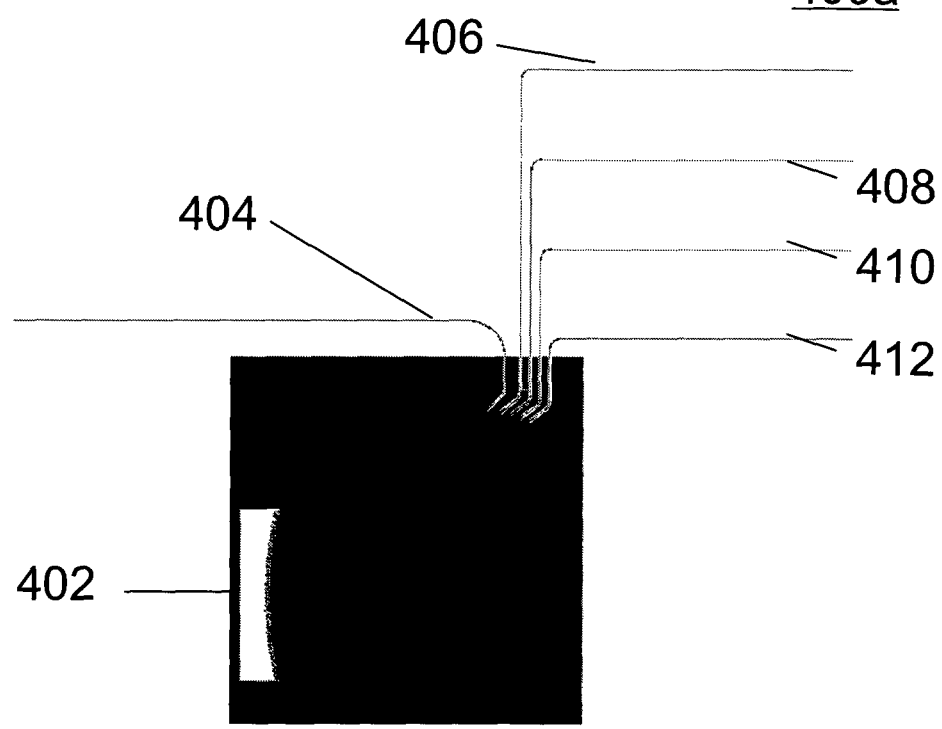
FIG. 4A shows a design of a portion of the optical sensing system according to various embodiments.
Figure 4B:
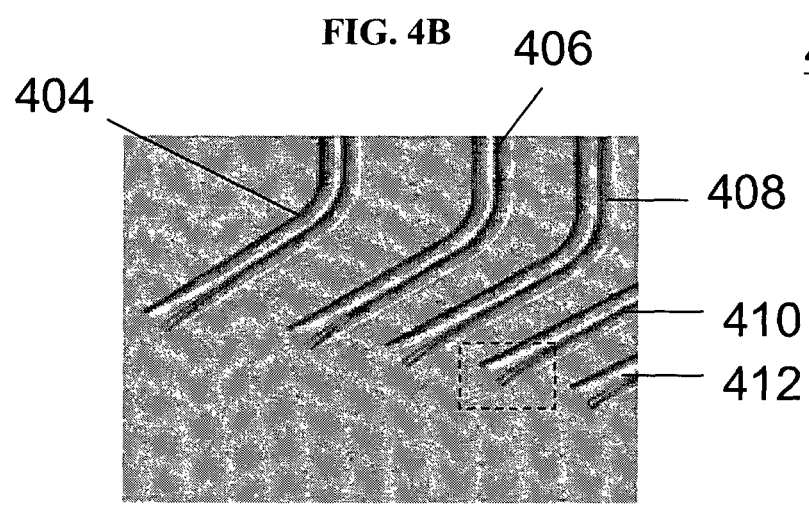
FIG. 4B is a scanning electron microscopy (SEM) image of the channel waveguides indicated in FIG. 4A according to various embodiments.
Figure 4C:
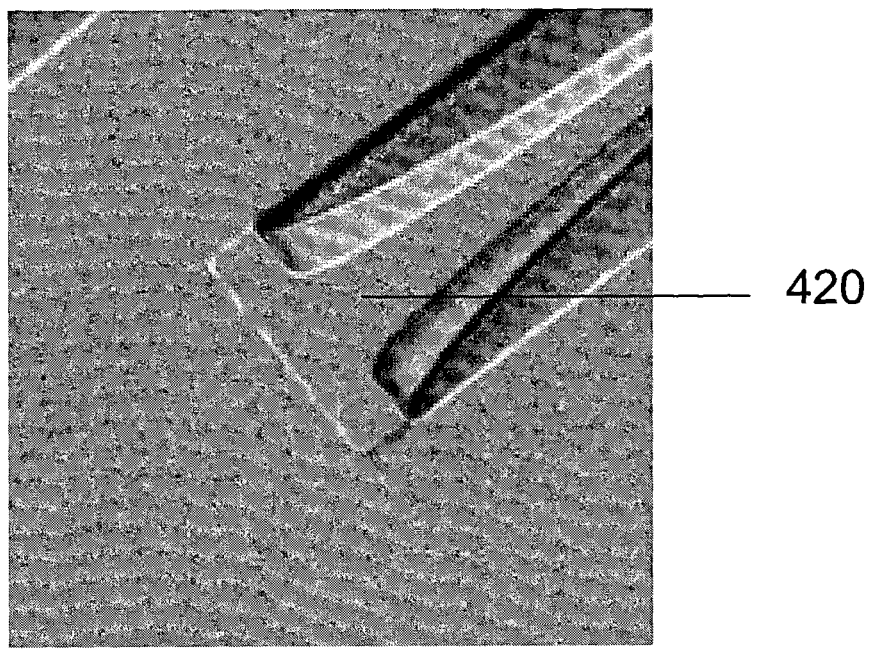
FIG. 4C is a SEM image of a mode converter for coupling between a slab waveguide and a channel waveguide according to various embodiments.
Figure 4D:
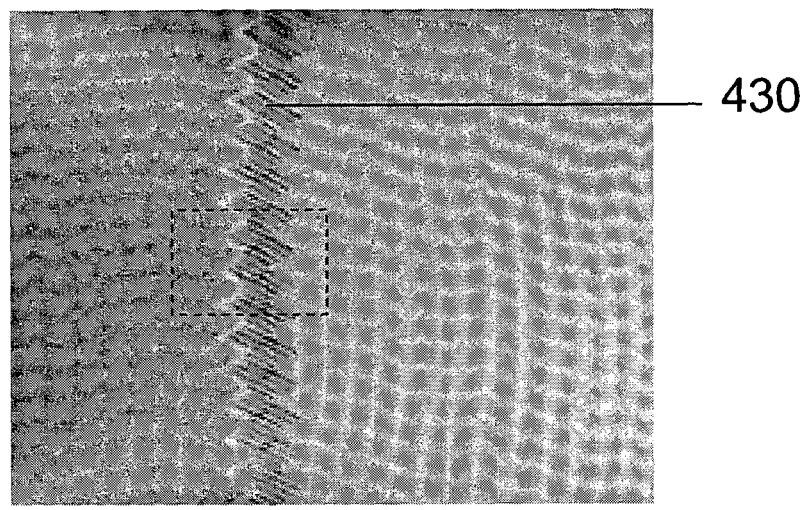
FIG. 4D is a SEM image of a concave grating with bragg gratings according to various embodiments.
Figure 4E:
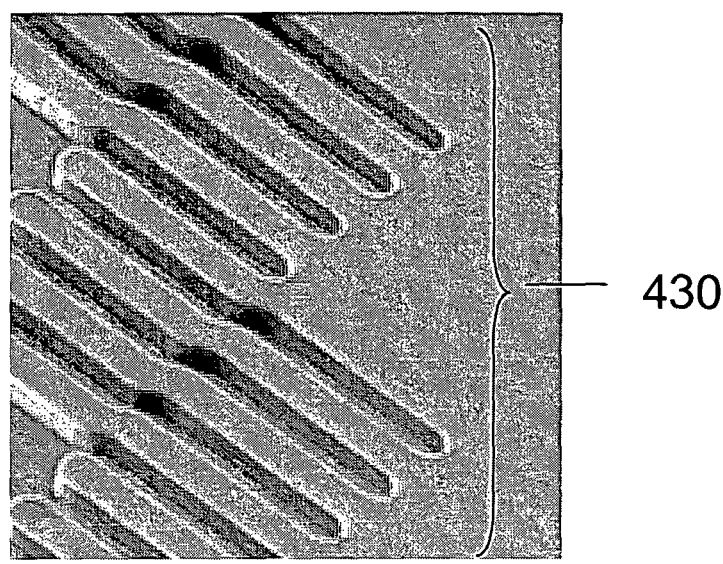
FIG. 4E is a SEM image of the bragg gratings.
Figure 4F:
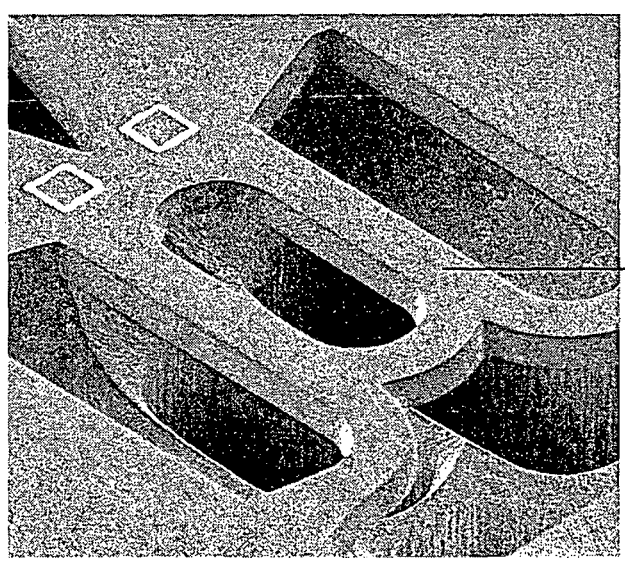
FIG. 4F is a SEM image of a microring resonator with underlying layer removed according to various embodiments.
Figure 4G:
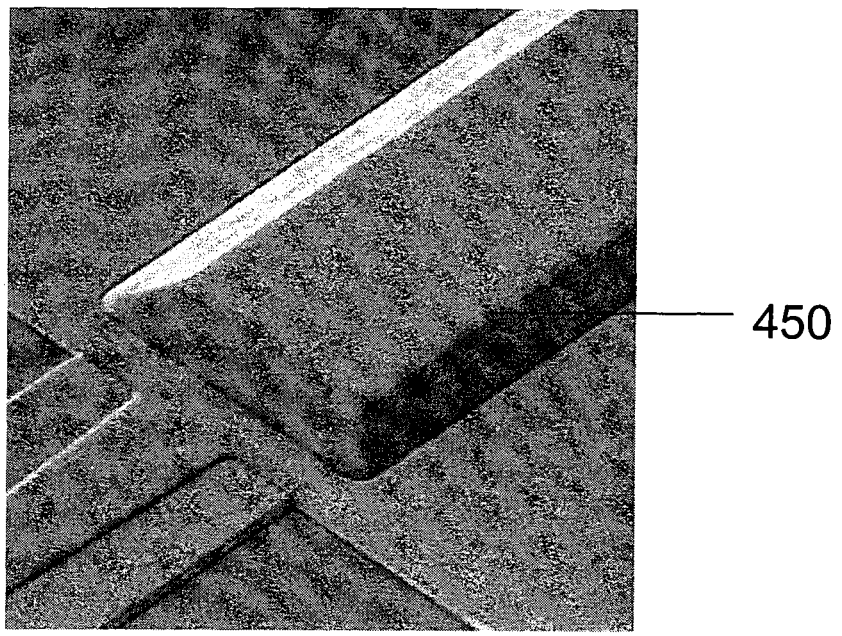
FIG. 4G is a SEM image of a germanium (Ge) photodetector according to various embodiments.
Figure 4H:
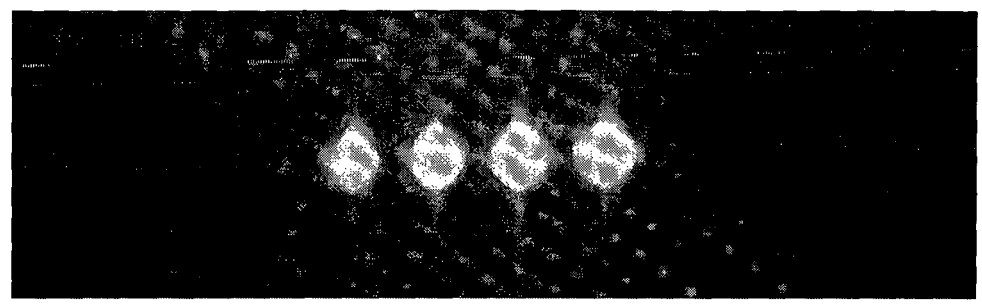
FIG. 4H is an image showing output light from the 4 waveguides.
Figure 4I:
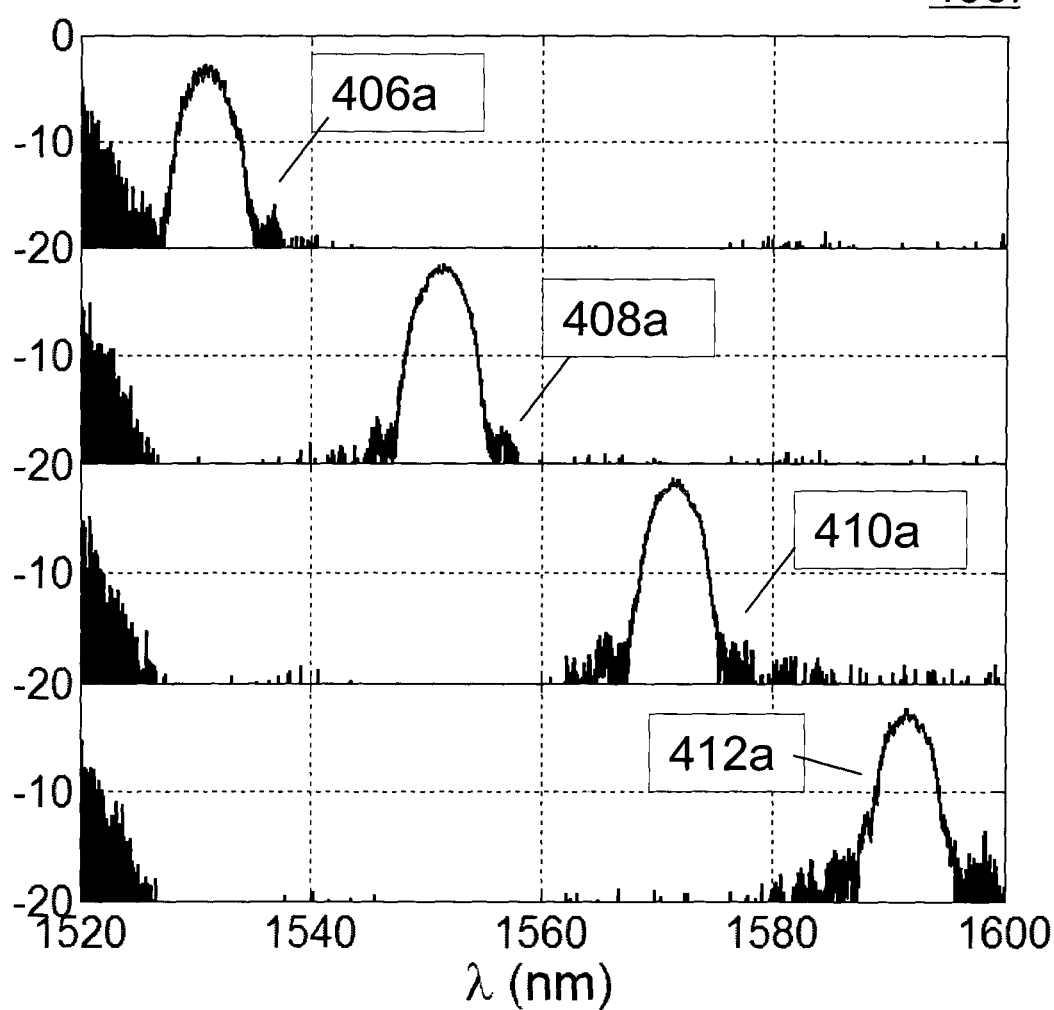
FIG. 4I is a graph of transmission (dB) against wavelength λ (nm) of the four output lights in FIG. 4H.
Figure 4J:
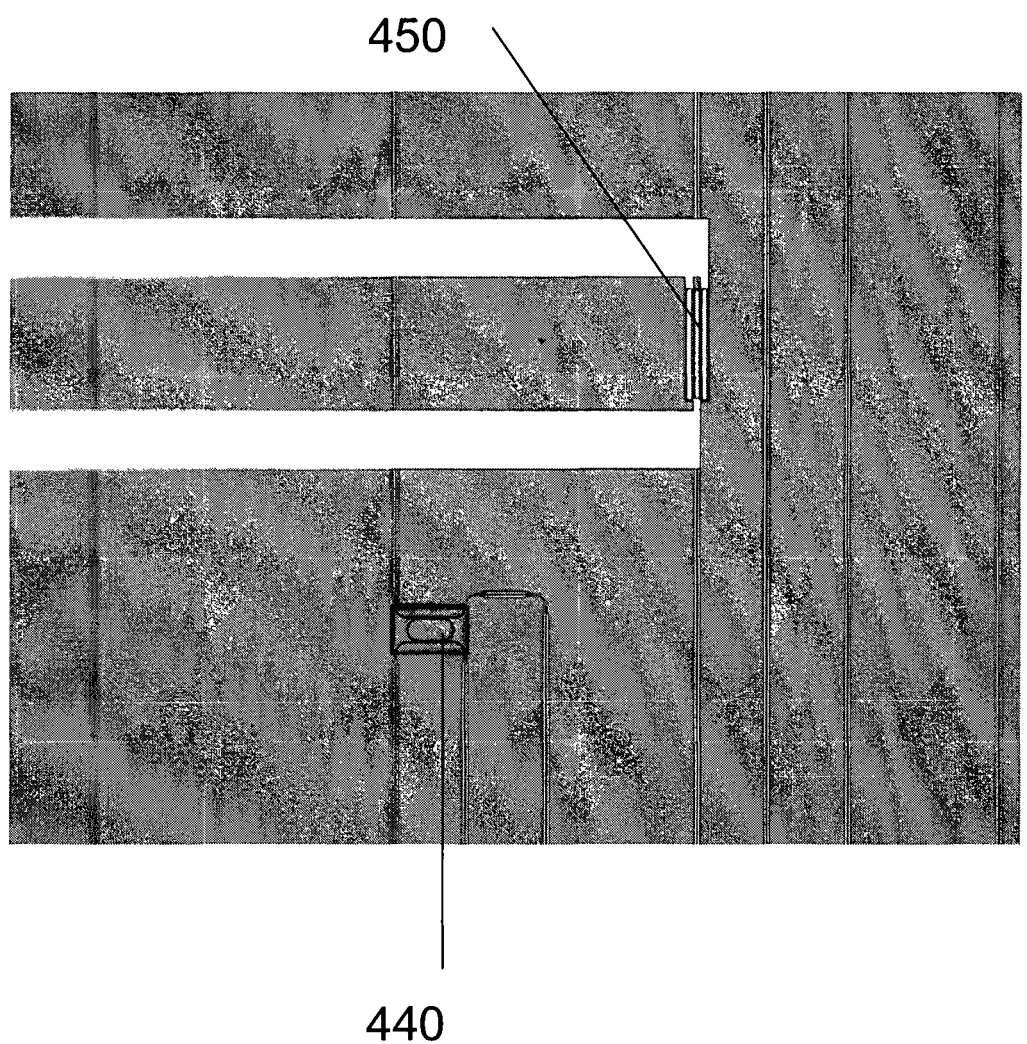
FIG. 4J is an image of a portion of the optical sensing system showing a microring resonator and the photodetector.
Figure 4K:
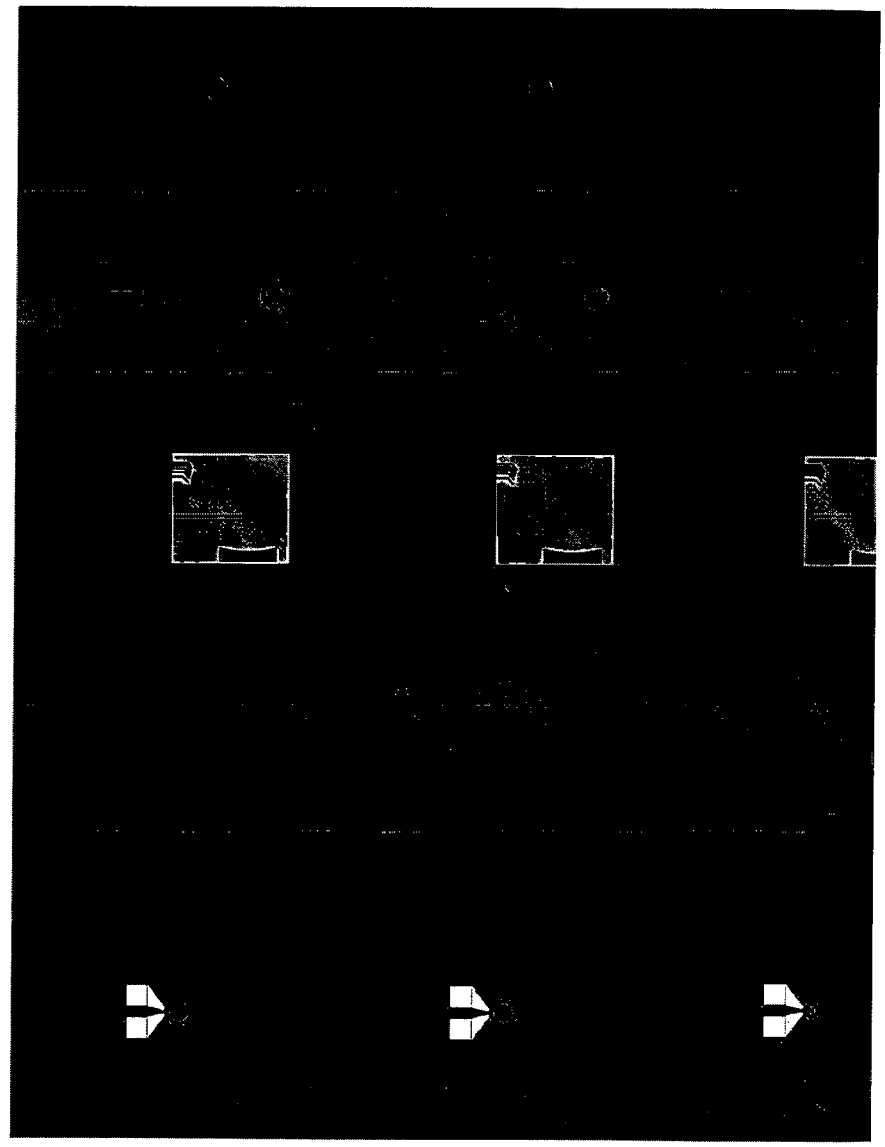
FIG. 4K is an image of three optical sensing systems fabricated on a substrate.

FIG. 4A shows a design 400a of a portion of the optical sensing system according to various embodiments. 402 is the concave grating for separating light into different ranges of wavelengths, i.e. the light separation element. 404 is the waveguide for coupling light to the concave grating 402. 406, 408, 410, 412 are waveguides for coupling sliced light from the concave grating 402. FIG. 4B is a scanning electron microscopy (SEM) image 400b of the waveguides 404, 406, 408, 410, 412 indicated in FIG. 4A according to various embodiments. FIG. 4C is a SEM image 400c of a mode converter 420 for coupling between a slab waveguide and a channel waveguide according to various embodiments FIG. 4D is a SEM image 400d of a concave grating with bragg gratings 430 according to various embodiments. FIG. 4E is a SEM image 400e of the bragg gratings 430. FIG. 4F is a SEM image 400f of a microring resonator 440 with underlying layer removed according to various embodiments. FIG. 4G is a SEM image 400g of a germanium (Ge) photodetector 450 according to various embodiments. FIG. 4H is an image showing output light from the 4 waveguides 406, 408, 410 and 412. FIG. 4I is a graph 400i of transmission (dB) against wavelength λ(nm) of the four output lights in FIG. 4H. Waveform 406a is from waveguide 406, waveform 408a is from waveguide 408, waveform 410a is from waveguide 410 and waveform 412a is from waveguide 412. FIG. 4J is an image 400j of a portion of the optical sensing system showing microring resonator 440 and the photodetector 450. FIG. 4K is an image 400k of three optical sensing systems fabricated on a substrate.

Figure 5A:
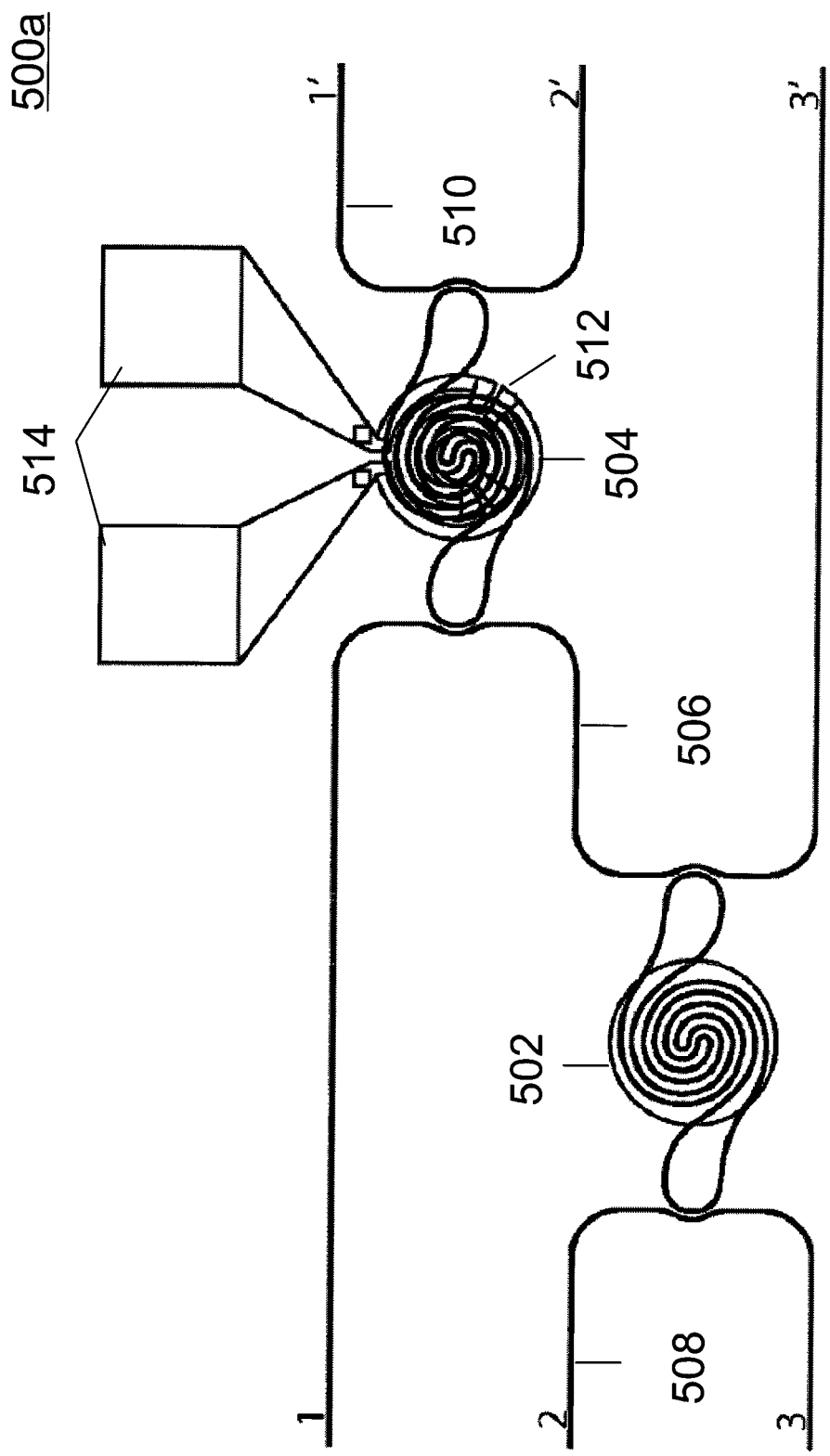
FIG. 5A shows a schematic view of an optical sensing system according to various embodiments.

FIG. 5A shows a schematic view 500a of an optical sensing system 500a according to various embodiments. The optical sensing system 500a may include a sensing resonator 502 and a tracing resonator 504. The optical sensing system 500a further includes a coupling optical waveguide 506 coupled between the sensing resonator 502 and the tracing resonator 504. The optical sensing system 502 may further include an input waveguide 508 configured to guide an input light, for example from a wideband or broadband source (not shown). The input waveguide 508 is coupled to the sensing resonator 502. The optical sensing system 500a may further include an output waveguide 510 coupled to the tracing resonator 504, the output waveguide 510 being configured to output light received from the resonator the tracing resonator 504 to a detector (not shown). The optical sensing system or tracing resonator 504 may further include a heater or thermal heater 512 formed or arranged in proximity to supply heat to the tracing resonator 504, for instance to change the refractive index or effective refractive index of the tracing resonator in order to trace the effective refractive change of the sensing resonator 502. The heater or thermal heater 512 may include a pair of electrodes 514. The optical system 502 may include three input ports and three output ports in order to measure the optical properties of both resonators. The resonators may be microring resonators. A light may be provided to port 1 of waveguide 506 and the light from port 1' of waveguide 510 may be monitored to determine the 'drop' status of the tracing resonator 504. A light may be provided to port 3 of the waveguide 508 and the light from port 3' of the waveguide 506 may be monitored to determine the 'drop' status of the sensing resonator 502. A light may be provided to port 1 of the waveguide 506 and the light from port 3' of waveguide 506 may be monitored to determine the 'through' status of the tracing resonator 504 and the sensing resonator

Figure 5B:
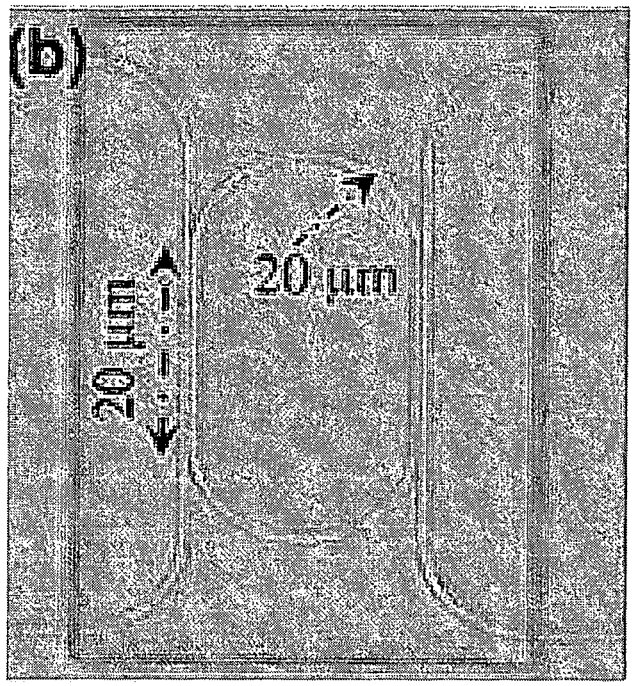
FIG. 5B is an image of a sensing resonator according to various embodiments.
Figure 5C:
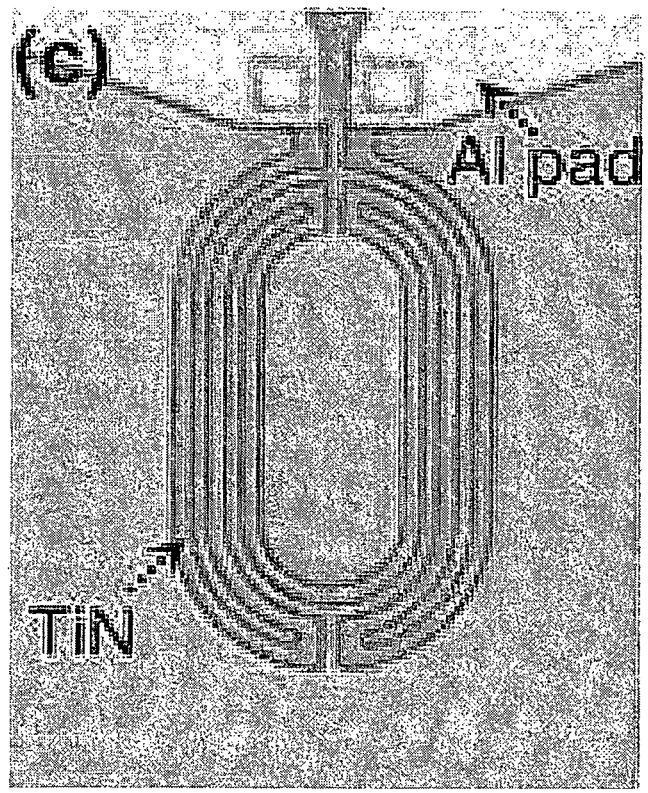
FIG. 5C is an image of a tracing resonator according to various embodiments.
Figure 5D:
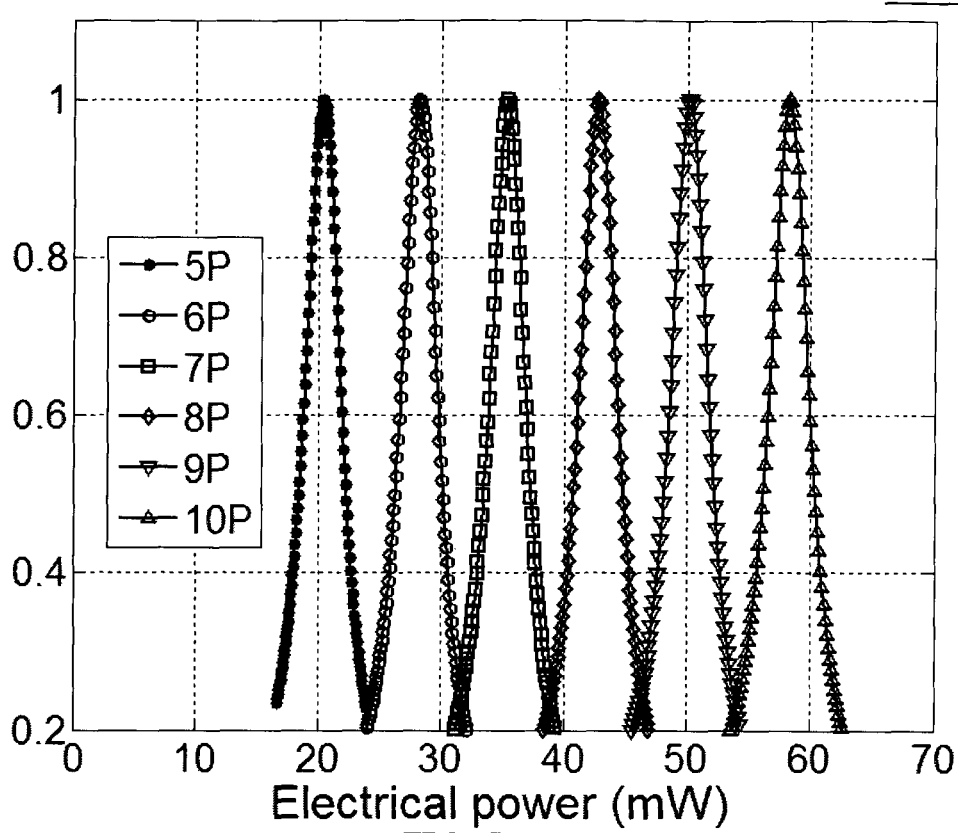
FIG. 5D is a graph of optical power (normalized) against electrical power (mW) illustrating the measured optical responses of sensing resonators having different refractive index changes induced by different polymer periods upon electrical power supply to the tracing resonator.
Figure 5E:
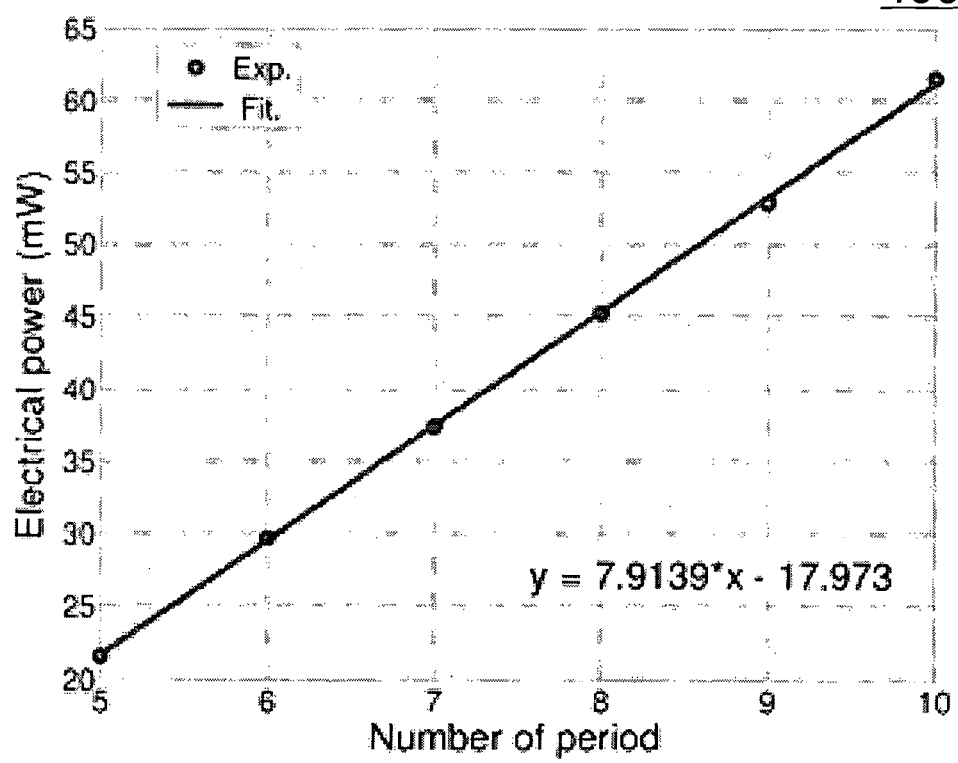
FIG. 5E is a graph of electrical power (mW) against polymer period illustrating the linear fitting of electrical power supplied (corresponding to maximum optical response) by the tracing resonator as a function of polymer periods.
Figure 5F:
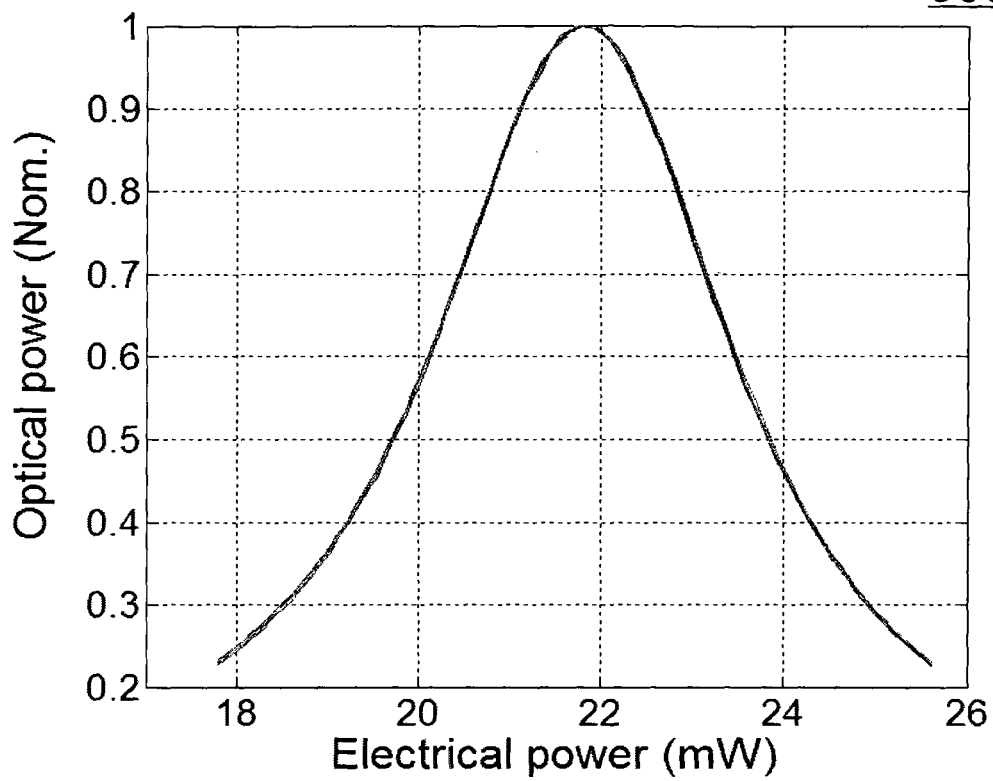
FIG. 5F is a graph of optical power (normalized) against electrical power (mW) obtained when the optical sensing system is used to contact a sample.
Figure 5G:
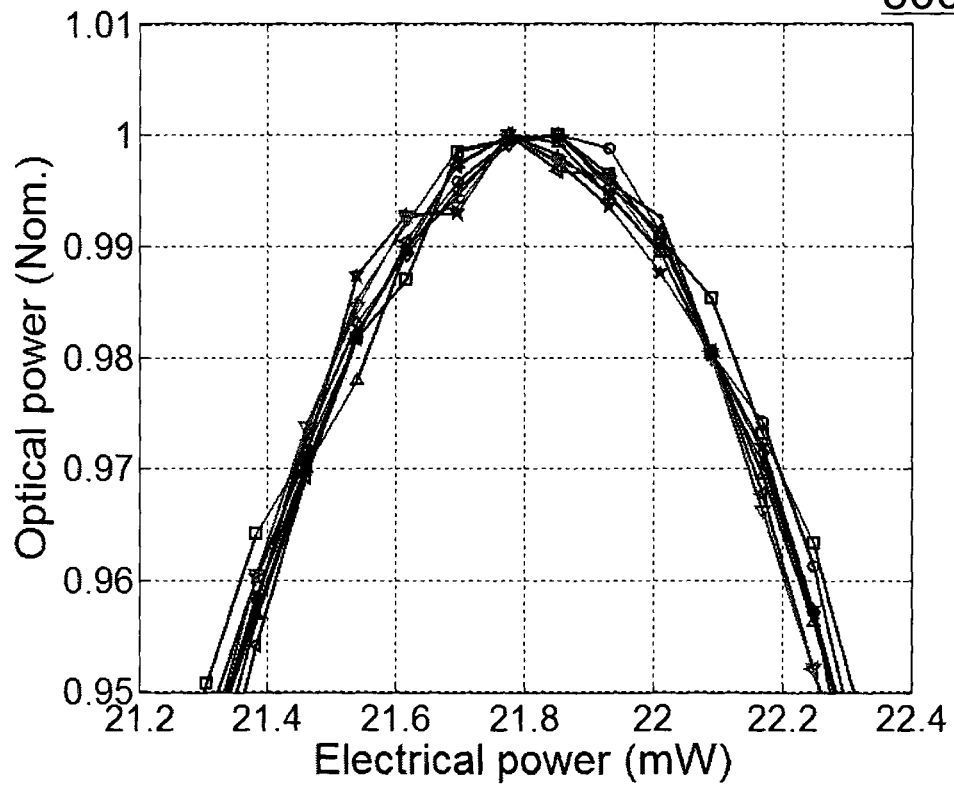
FIG. 5G is a graph of optical power (normalized) against electrical power (mW) obtained during different experimental runs.
Figure 5H:
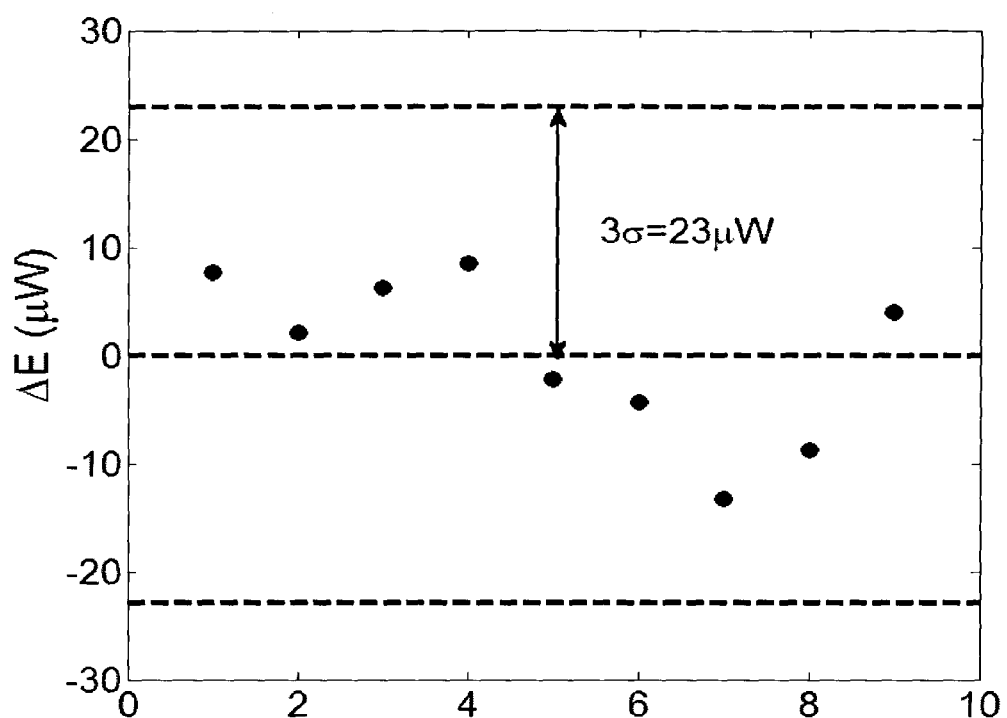
FIG. 5H is a graph illustrating the difference in electrical power (in µW) to obtain the same optical response in different experimental runs.

502. A light may be provided to port 2 of the waveguide 508 and the light from port 2' of the waveguide 510 may be monitored for sensing a sample according to various embodiments. FIG. 5B is an image 500b of a sensing resonator 502 according to various embodiments. FIG. 5C is an image 500c of a tracing resonator 504 according to various embodiments. A preliminary demonstration has been carried out showing the electrical tracing of the refractive index change. The refractive index is varied through different polymer periods. FIG. 5D is a graph 500d of optical power (normalized) against electrical power (mW) illustrating the measured optical responses of sensing resonators having different refractive index changes induced by different polymer periods upon electrical power supply to the tracing resonator. FIG. 5E is a graph 500e of electrical power (mW) against polymer period illustrating the linear fitting of electrical power supplied (corresponding to maximum optical response) by the tracing resonator as a function of polymer periods. By reading the refractive index induced by the change in electrical power, the change in refractive index induced by the change in polymer period may be directly read out. FIG. 5F is a graph 500f of optical power (normalized) against electrical power (mW) obtained when the optical sensing system is used to contact a sample. FIG. 5G is a graph 500g of optical power (normalized) against electrical power (mW) obtained during different experimental runs. FIG. 5H is a graph 500h illustrating the difference in electrical power (in µW) to obtain the same optical response in different experimental runs.

Figure 6A:
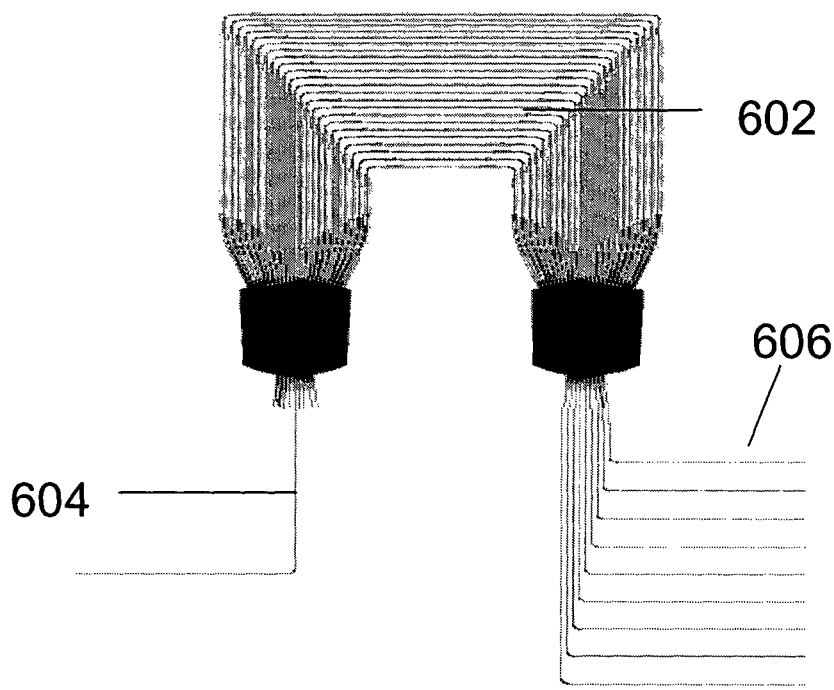
FIG. 6A is a diagram showing a portion of a optical sensing system having a 8 channel arrayed waveguide grating (AWG) according to various embodiments.
Figure 6B:
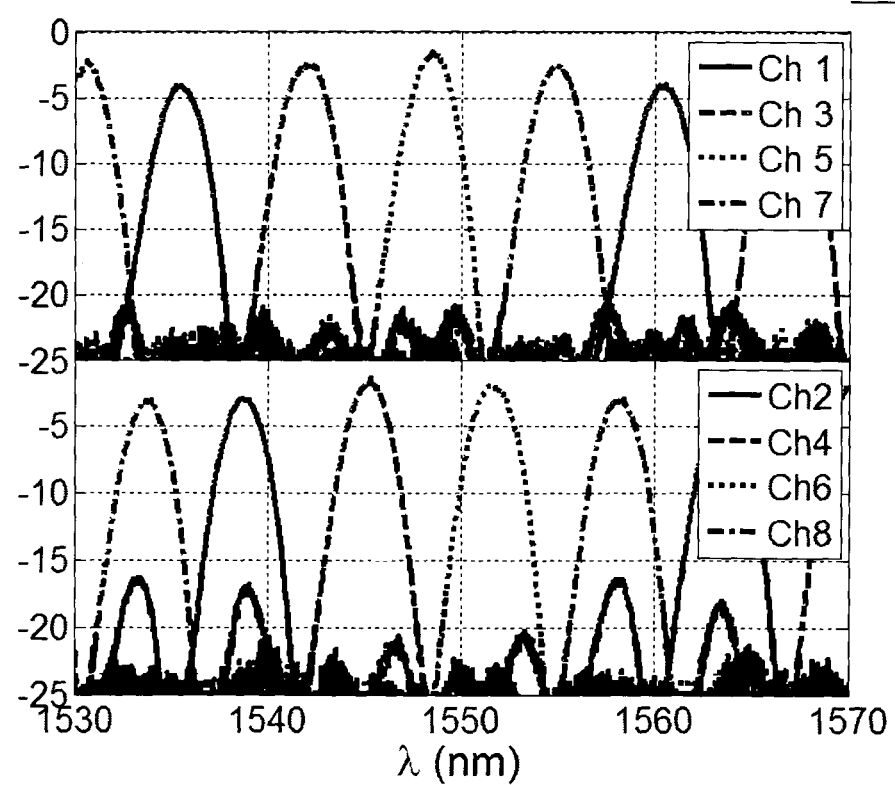
FIG. 6B is a graph of optical loss (dB) against wavelength (nm) illustrating the measured transmission spectra of 8 output ports of the AWG shown in FIG. 6A according to various embodiments using a ASE light source.

FIG. 6A is a diagram 600a showing a portion of a optical sensing system having a 8 channel arrayed waveguide grating (AWG) 602 according to various embodiments. The optical sensing system may include a waveguide 604 for coupling light from a broadband source to the AWG 602. The optical sensing system may also include 8 waveguides 606 for coupling sliced light from the AWG. FIG. 6B is a graph 600b of optical loss (dB) against wavelength (nm) illustrating the measured transmission spectra of 8 output ports of the AWG shown in FIG. 6A according to various embodiments using a ASE light source.

FIG. 7 is a schematic 700 illustrating a method of determining a change in an refractive index in an optical sensing system according to various embodiments. The method may include, in 702, separating an input light into a plurality of sliced lights. The method may further include, in 704, coupling one sliced light of the plurality of sliced lights though a first resonator of a plurality of first resonators to one detector of a plurality of detectors of the optical sensing system. The method may also include, in 706, placing a sample in contact with the first resonator. The method may additionally include, in 708, measuring a change in an intensity of the sliced light by the detector due to the sample being placed in contact with the first resonator. The change in intensity may be based on a change in a difference between a resonant wavelength of the first resonator and a resonant wavelength of a second resonator. The method may further include, in 710, determining the change in an effective refractive index of the first resonator based on the change in the intensity of the sliced light.

In other words, an input light may be separated into a plurality of sliced lights. One of the sliced lights may be coupled to one first resonator. The sliced light may be coupled directly or indirectly to a first resonator. The sliced light may then coupled directly or indirectly to a detector. The first resonator may be placed in contact with the sample. The change in an intensity of the sliced light may then be measured by the detector. The peaks detected by the detector may be caused by the interaction of a resonant wavelength of the first resonator and a resonant wavelength of the second resonator. As such, the change in intensity may vary as the resonant wavelength of the first resonator shifts relative to the resonant wavelength of the second resonator. The shift in the resonant wavelength of the first resonator may be due to a change in the effective refractive index of the first resonator as a result of the first resonator being placed in contact with the sample. The change in effective refractive index of the first resonator may then be determined based on the change in intensity of the sliced light.

The sliced light may have a range of wavelengths that is a subset of the range of wavelengths of the input light. The input light may be separated into the plurality of sliced light by a light separation element. Each sliced light may have a different range of wavelengths. A sliced light may have an overlapping or non-overlapping range of wavelengths with a further sliced light.

Various embodiments may relate to determining an effective index of a sample by adjusting the second resonator. In various embodiments, the output intensity may initially be at the predefined value. The first resonator is used to contact a sample such as a chemical or biological sample. As a result, the intensity may change due to a change in the effective refractive index of the first resonator. The change in effective refractive index of the first resonator may be due to a change in a refractive index of a cladding of the first resonator.

By adjusting the current or voltage applied to a second resonator until the output intensity is again at the predefined value, the change in refractive index of the first resonator may be determined. The current or voltage applied to the second resonator may be used to determine the change in refractive index of the first resonator. Consequently, the sample may be identified based on the change in refractive index of the first resonator. In other words, the method may also include defining a predefined value. The method may further include measuring the change in the intensity of the sliced light (after placing the sample in contact with the first resonator) by adjusting the voltage or current applied to the second resonator such that the intensity is again at the predefined value. The change in intensity of the sliced light may be measured indirectly by measuring the voltage or current applied to the second resonator such that the intensity of the sliced light is again at the predefined value. The change in refractive index may be determined based on the current or voltage applied to the second resonator.

In various embodiments, the predefined value may be a maximum intensity. The predefined value may correspond when the wavelength of light coupled to the first resonator is at the resonant wavelength of the first resonator and the wavelength of the first resonator and the wavelength of light coupled to the second resonator is at the resonant wavelength of the second resonator. The first resonator and the second resonator may be configured to have the same separation between successive resonant wavelengths.

Various embodiments may relate to determining an effective index of a sample by determining the change in resonant wavelength of the first resonator. In various embodiments, the method may further include determining the difference between the resonant wavelength of the first resonator and the resonant wavelength of the second resonator based on the intensity of the sliced light. Determining the change in an effective refractive index of the first resonator may be based on the change in the difference between the resonant wavelength of the first resonator and the resonant wavelength of the second resonator.

Determining a change on the difference between the resonant wavelength of the first resonator and the resonant wavelength of the second resonator may include fixing the resonant wavelength of the second resonator and determining the change in resonant wavelength of the first resonator. The change in resonant wavelength of the first resonator may be determined based on the change in intensity of the sliced light. In other words, the method may include fixing the second resonator (i.e. keeping the voltage or current applied to the second resonator constant). The method may include determining the change in resonant wavelength of the first resonator based on the change in intensity of the sliced light. The change in the effective refractive of the first resonator may be determined based on the change in resonant wavelength of the first resonator. The determination in the change in the effective refractive of the first resonator may be carried out by a calculation or by looking up a correlation table etc.

In various embodiments, the second resonator may be coupled between the first resonator and the detector. The sliced light may be coupled from the first resonator to the second resonator and from the second resonator to the detector. In various embodiments, the first resonator may be coupled between the second resonator and the detector. The sliced light may be coupled from the second resonator to the first resonator and from the first resonator to the detector.

In various embodiments, the second resonator may be coupled between the light source and the light separation element. The input light may be coupled to the second resonator from the light source to the second resonator and from the second resonator to the light separation element. At the light separation element, the input light may be separated into a plurality of sliced lights, one sliced light of the plurality of sliced light may then be coupled to the first resonator. The sliced light may then be coupled to the detector.

In various embodiments, the sliced light may be coupled to an input port of the first resonator. The sliced light may be outputted from the drop port of the first resonator. Similarly, the sliced light or input light may be coupled to an input port of the second resonator. The sliced light or input light may be outputted from the drop port of the second resonator.

Various embodiments may apply to the optical sensing system shown in FIG. 2A. In various embodiments, the method may further include coupling a further sliced light of the plurality of sliced lights though a further first resonator of the plurality of first resonators to a further detector of a plurality of detectors of the optical sensing system. Coupling the further sliced light of the plurality of sliced lights through a further first resonator of the plurality of first resonators to a further detector of the plurality of further detectors may include coupling the further sliced light to the further first resonator and coupling the sliced light from the further first resonator to the further detector. In particular, coupling the further sliced light of the plurality of sliced light through a further first resonator of the plurality of first resonators to a further detector of the plurality of further detectors may include coupling the further sliced light to an input port of the further resonator and coupling the further sliced light from a drop port of the further resonator to the detector.

Various embodiments may relate to determining change in one or more effective indexes of one or more first resonators by using a reference sample. In various embodiments, the method may include placing the further first resonator in contact with a reference sample such that a change in further effective refractive index of the further first resonator is predetermined. The method may also include measuring a change in a further intensity of the further sliced light by the further detector due to the reference sample being placed in contact with the further first resonator. Determining the change in the effective refractive index of the first resonator may be further based on the predetermined change in the further effective refractive index and the change in the further intensity of the further sliced light by the further detector. In other words, since the change in the further effective refractive index of the reference sample is already known, the known further effective refractive index of the reference sample as well as the measured change in the further intensity may be used (together with the measured change in the intensity measured by the detector) to determine the refractive index of the (test) sample. The remaining respective sliced lights of the plurality of sliced lights may be coupled through remaining respective first resonators to remaining respective detectors. The remaining respective first resonators may be brought to contact with other samples to determine the respective refractive indexes of the other samples. In this manner, various embodiments may be used to sense multiple samples at the same time. Various embodiments may be used to sense multiple test samples using a reference sample.

Various embodiments may relate to determining a change in a further effective index of a further first resonator by adjusting the second resonator. In various embodiments, the method may include coupling a further sliced light through a further first resonator to a further detector. The method may also include placing a further sample in contact with a further first resonator. The method may also include measuring a further intensity by the further detector due to the further sample being place in contact with the further first resonator. The method may also include defining a further predefined value. The method may further include measuring the change in the further intensity of the further sliced light (after placing the sample in contact with the first resonator) by adjusting the voltage or current applied to the second resonator such that the further intensity is again at the predefined value. The change in the further refractive index may be determined based on the current or voltage applied to the second resonator.

Various embodiments may relate to determining a further effective index of a further sample by determining the change in a resonant wavelength of a further first resonator. In other various embodiments, the method may include coupling a further sliced light through a further first resonator to a further detector. The method may also include placing a further sample. The method may also include measuring a change in a further intensity by the further detector due to the further sample being placed in contact with the further first resonator. The change in further intensity may be based on the change in the difference between the resonant wavelength of the further first resonator and the resonant wavelength of the second resonator. The method may also include determining a change in a further refractive index of the further first resonator based on the change in a further intensity of the further sliced light.

The method may include fixing the second resonator (i.e. keeping the voltage or current applied to the second resonator constant). The method may include determining the change in the resonant wavelength of the further first resonator based on the change in further intensity of the further sliced light. The change in the further effective refractive of the further first resonator may be determined based on the change in resonant wavelength of the further first resonator. The determination in the change in the further effective refractive of the further first resonator may be carried out by calculation or by looking up a correlation table etc.

In various embodiments, the further sliced light may have a range of wavelengths different from the range of wavelengths of the sliced light. The range of wavelengths of the further sliced light may or may not overlap with the range of wavelengths of the sliced light.

Various embodiments may apply to the optical sensing system shown in FIG. 3. In various embodiments, the method may further include coupling a further sliced light of the plurality of sliced light to a further second resonator. The method may also include further coupling the further sliced light from the further second resonator through a further first resonator of the plurality of first resonators to a further detector of a plurality of detectors of the optical sensing system. The method may additionally include measuring a change in intensity of the further sliced light by the further detector due to a further sample being placed in contact with the further first resonator.

Coupling the further sliced light from the further second resonator through a further first resonator of the plurality of first resonators to a further detector of a plurality of detectors of the optical sensing system may include coupling the further sliced light from the further second resonator to the further first resonator and from the further first resonator to the further detector. In particular, the sliced light may be coupled from a drop port of the further second resonator to the input port of the further first resonator and from a drop port of the further first resonator to the further detector.

Coupling the further sliced light to the further second resonator may include coupling the sliced light to an input port of the further second resonator.

In various embodiments, the positions of the first resonator and the second resonator may be interchangeable. The positions of the further first resonator and the further second resonator may be interchangeable. In other words, the first resonator may be coupled between the second resonator and the detector. The sliced light may be coupled to the first resonator. The sliced light may be coupled from the first resonator to the second resonator and from the second resonator to the detector.

The method may further include coupling a further sliced light of the plurality of sliced lights to the further first resonator. The method may also include further coupling the further sliced light from the further first resonator through the further second resonator to the further detector. The method may additionally include measuring a further output intensity by the further detector.

Various embodiments may relate to determining one or more further effective refractive indexes of a sample or further samples by determining the change in a resonant wavelength of a first resonator or further first resonators. In various embodiments, the method may include coupling a sliced light or further respective sliced lights through a first resonator or further respective first resonators to a detector or further respective detectors. The method may also include placing a sample or further respective samples in contact with a first resonator or further respective resonators. The method may also include measuring a change in an intensity or further respective intensities by the detector or further respective detectors due to the sample or further respective sample being placed in contact with the first resonator or further respective first resonators. The change in intensity or further respective intensities may be based on the change in the difference or respective differences between the resonant wavelength or respective resonant wavelength of the first resonator/further respective first resonators and the resonant wavelength or respective resonant wavelength of the second resonator/further respective second resonators. The method may also include determining a change in a further refractive index of the first resonator/further respective first resonators based on the change in a intensity/further respective intensity of the sliced light/further respective sliced light.

The method may include fixing the second resonator/further respective second resonators (i.e. keeping the voltage or current applied to the second resonator/respective further resonators constant). The method may include determining the change in the resonant wavelength or respective resonant wavelengths of the first resonator/further respective first resonators based on the change in the intensity/further respective intensity of the sliced light/further respective sliced light. The change in the effective refractive index/further effective refractive of the first resonator/further respective first resonator may be determined based on the change in the resonant wavelength or respective resonant wavelengths of the first resonator/further respective first resonators. The determination in the change in the effective refractive index/further effective refractive indexes of the first resonator/further respective first resonators may be carried out by calculation or by looking up a correlation table etc.

Various embodiments may relate to determining one or more effective refractive indexes of one or more sample by adjusting one or more second resonators. In various embodiments, the sliced light may include a wavelength that is equal or near the resonant wavelength of the first resonator. The second resonator may be configured or adjusted such that the resonant wavelength of the second resonator is near or at the resonant wavelength of the first resonator. The first resonator may then be brought into contact with a sample. The effective refractive index of the first resonator may change in response to a refractive index of a cladding of the first resonator. The refractive index of the cladding of the first resonator may change as a result of the first resonator being brought into contact with the sample. The resonant wavelength of the first resonator may shift such that the shifted resonant wavelength of the first resonator is now no longer near or at the resonant wavelength of the second resonator and the intensity of the sliced light measured by the detector decreases. In order to increase or maximize the intensity of the sliced light, the second resonator may be tuned via electro-optic or thermo-optic effect to shift the resonant wavelength of the second resonator such that the shifted resonant wavelength of the second resonator again coincides with or is near the shifted resonant wavelength of the first resonator.

Similarly, a further sliced light may include a wavelength that is equal or near the resonant wavelength of the further first resonator. The further second resonator may be configured or adjusted such that the resonant wavelength of the further second resonator is near or at the resonant wavelength of the further first resonator. The further first resonator may then be brought into contact with a further sample. The further sample may be the same or different from the sample. The effective refractive index of the further first resonator may change in response to a change in refractive index of a cladding of the further first resonator. The refractive index of the cladding of the further first resonator may change as a result of the further first resonator being brought into contact with the further sample. The resonant wavelength of the further first resonator may shift such that the shifted resonant wavelength of the first resonator is now no longer near or at the resonant wavelength of the further second resonator and the intensity of the further sliced light measured by the further detector decreases. In order to increase or maximize the intensity of the further sliced light, the further second resonator may be tuned via electro-optic or thermo-optic effect to shift the resonant wavelength of the further second resonator such that the shifted resonant wavelength of the further second resonator again coincides with or is near the shifted resonant wavelength of the further first resonator.

In other words, the method may also include defining one or more predefined values. The method may further include measuring the change in the respective intensities of the sliced light/further sliced lights (after placing the sample/further samples in contact with the first resonator/further first resonators) by adjusting the voltage or current applied to each second resonator such that the respective intensities is again at the predefined value or values. The change in the one or more refractive indexes may be determined based on the current or voltage applied to each second resonator. One refractive index may be determined based on the current or voltage applied to one second resonator.

As such, multiple samples may be sensed using the optical sensing system at the same time. Multiple samples may be sensed using multiple branches of the optical sensing system at the sample time. Each branch may include a first resonator, a second resonator and a detector. The positions of the first resonator and the second resonator in each branch may be interchangeable.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An optical sensing system, the optical sensing system comprising:
   a light separation element configured to separate an input light into a plurality of sliced lights, each sliced light of the plurality of sliced lights having a different range of wavelengths;
   a plurality of first resonators, each first resonator of the plurality of first resonators configured to receive one respective sliced light of the plurality of sliced lights, wherein an effective refractive index of each first resonator is changeable in response to a change in a refractive index of a cladding of the respective first resonator; and wherein at least one first resonator of the plurality of first resonators is configured to contact a sample so that a refractive index of a cladding of the at least one first resonator is changed as a result of the at least one first resonator brought into contact with the sample;
   at least one second resonator coupled to the plurality of first resonators;
   a plurality of detectors, wherein one respective detector of the plurality of detectors is configured to measure a respective intensity of the respective sliced light based on a difference between a resonant wavelength of each first resonator and a resonant wavelength of the at least one second resonator;
   wherein the difference between the resonant wavelength of each first resonator and the resonant wavelength of the at least one second resonator is based on the effective refractive index of each first resonator.

2. The optical sensing system according to claim 1, wherein the resonant wavelength of the second resonator is adjustable to a current or voltage applied to the second resonator.

3. The optical sensing system of claim 2, wherein each second resonator comprises a thermal heater, and wherein the current or voltage being adjustable in response to the change in the effective refractive index of the first resonator is applied to the heater.

4. The optical sensing system according to claim 1, wherein the plurality of first resonators is coupled to the light separation element such that each first resonator of the plurality of first resonators is configured to receive one respective sliced light of the plurality of sliced lights.

5. The optical sensing system according to claim 4, the optical sensing system further comprising:
   a plurality of channel waveguides, each first resonator of the plurality of first resonators coupled to one respective channel waveguide of the plurality of channel waveguides;
   wherein the respective channel waveguide is configured to couple the respective sliced light between the light separation element and the respective first resonator.

6. The optical sensing system according to claim 4, the optical sensing system further comprising:
   a plurality of output waveguides;
   wherein one respective output waveguide of the plurality of output waveguides is coupled to each first resonator, the respective output waveguide configured to carry the respective sliced light from each first resonator; and
   wherein the respective detector is coupled to the respective output waveguide; wherein the respective detector is configured to receive the respective sliced light from the respective output waveguide.

7. The optical sensing system according to claim 4, wherein the respective intensity of the respective sliced light is based on a respective difference between a respective resonant wavelength of each first resonator and the resonant wavelength of the second resonator; wherein the respective difference between the respective resonant wavelength of each first resonator and the resonant wavelength of the second resonator is based on a respective effective refractive index of the respective first resonator.

8. The optical sensing system according to claim 7, wherein the respective effective refractive index of each first resonator is changeable in response to a change in a respective refractive index of a respective cladding of each first resonator.

9. The optical sensing system according to claim 4, wherein the optical sensing system further comprises a coupling waveguide coupling the second resonator and the light separation element.

10. The optical sensing system according to claim 9, the optical sensing system further comprising:
    an optical broadband source; and
    an input waveguide coupling the optical broadband source to the second resonator.

11. The optical sensing system according to claim 1, the optical sensing system further comprising:
    one or more further second resonators such that the optical sensing system comprises a plurality of second resonators, the plurality of second resonators coupled to the light separation element such that each second resonator of the plurality of second resonators is configured to receive one respective sliced light of the plurality of sliced light.

12. The optical sensing system according to claim 11, wherein one respective first resonator of the plurality of first resonators coupled to each second resonator such that the respective first resonator receives the respective sliced light from each second resonator.

13. The optical sensing system according to claim 12, the optical sensing system further comprising:
a plurality of coupling waveguides;
wherein one respective coupling waveguide of the plurality of coupling waveguides couples between each second resonator and the respective first resonator, the respective coupling waveguide configured to carry the respective sliced light from each second resonator to the respective first resonator.

14. The optical sensing system according to claim 11, the optical sensing system further comprising:
a plurality of output waveguides;
wherein one respective output waveguide of the plurality of output waveguides is coupled to the respective first resonator, the respective output waveguide configured to carry the respective sliced light from the respective first resonator; and
wherein the respective detector is coupled to the respective output waveguide; wherein the respective detector is configured to receive the respective sliced light from the respective output waveguide.

15. The optical sensing system according to claim 11, wherein the respective intensity of the respective sliced light is based on a respective difference between a respective resonant wavelength of the respective first resonator and a respective resonant wavelength of each second resonator;
wherein the respective difference between the respective resonant wavelength of the respective first resonator and the respective resonant wavelength of each second resonator is based on a respective effective refractive index of the respective first resonator.

16. The optical sensing system according to claim 15, wherein the respective effective refractive index of the respective first resonator is changeable in response to a change in a respective refractive index of a respective cladding of the respective first resonator.

17. The optical sensing system according to claim 11, the optical sensing system further comprising:
an optical broadband source; and
an input waveguide coupling the optical broadband source to the light separation element.

18. A method of determining a change in an effective refractive index of one first resonator of a plurality of first resonators in an optical sensing system, the method comprising:
separating an input light into a plurality of sliced lights, each sliced light of the plurality of sliced lights having a different range of wavelengths;
coupling one sliced light of the plurality of sliced lights through the one first resonator of the plurality of first resonators to one detector of a plurality of detectors of the optical sensing system;
coupling another sliced light of the plurality of sliced lights through another first resonator of the plurality of first resonators to another detector of the plurality of detectors of the optical sensing system;
placing a sample in contact with the one first resonator of the plurality of first resonators so that a refractive index of a cladding of the one first resonator is changed as a result of the one first resonator brought into contact with the sample;
placing a reference sample in contact with the another first resonator of the plurality of first resonators so that a refractive index of a cladding of the another first resonator is changed as a result of the another first resonator brought into contact with the reference sample;
measuring a change in an intensity of the one sliced light by the one detector due to the sample being placed in contact with the one first resonator of the plurality of first resonators, the change in intensity based on a change in a difference between a resonant wavelength of the one first resonator of the plurality of first resonators and a resonant wavelength of a second resonator;
measuring a change in a further intensity of the another sliced light due to the reference sample being placed in contact with the another first resonator of the plurality of first resonators; and
determining the change in an effective refractive index of the one first resonator of the plurality of first resonators based on the change in the intensity of the one sliced light, the change in the further intensity of the another sliced light, and a predetermined change in a further effective refractive index of the another first resonator of the plurality of first resonators.

* * * * *